(12) United States Patent
Leigh

(10) Patent No.: US 10,893,937 B2
(45) Date of Patent: Jan. 19, 2021

(54) MAGNET SUPPORT OF AN IMPLANT

(71) Applicant: Charles Roger Aaron Leigh, Macquarie University (AU)

(72) Inventor: Charles Roger Aaron Leigh, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 692 days.

(21) Appl. No.: 15/492,708

(22) Filed: Apr. 20, 2017

(65) Prior Publication Data
US 2018/0303602 A1    Oct. 25, 2018

(51) Int. Cl.
*A61F 2/18* (2006.01)
*H04R 25/00* (2006.01)

(52) U.S. Cl.
CPC ............. *A61F 2/18* (2013.01); *H04R 25/606* (2013.01); *A61F 2002/183* (2013.01); *A61F 2210/009* (2013.01); *H04R 2225/67* (2013.01)

(58) Field of Classification Search
CPC .................. A61F 2/18; A61F 2002/183; A61F 2210/009; H04R 2225/67; H04R 25/606
See application file for complete search history.

(56) References Cited

U.S. PATENT DOCUMENTS

| 7,386,143 | B2 | 6/2008 | Easter et al. | |
| 2004/0012470 | A1* | 1/2004 | Zimmerling | A61N 1/37 335/207 |
| 2005/0107870 | A1 | 5/2005 | Wang et al. | |
| 2008/0044049 | A1 | 2/2008 | Ho et al. | |
| 2009/0292338 | A1 | 11/2009 | Gordon et al. | |
| 2011/0270356 | A1 | 11/2011 | McKenzie et al. | |
| 2013/0004003 | A1 | 1/2013 | Tada | |
| 2013/0184804 | A1 | 7/2013 | Dalton | |
| 2015/0382114 | A1* | 12/2015 | Andersson | H04R 25/606 600/25 |
| 2017/0056631 | A1* | 3/2017 | Leung | H01F 41/026 |

FOREIGN PATENT DOCUMENTS

| AU | 2009101370 A4 | 3/2013 | |
| KR | 100859979 B1 | 9/2008 | |
| WO | 2015/065442 A2 | 5/2015 | |
| WO | 2016191429 A1 | 12/2016 | |
| WO | WO-2016191429 A1 * | 12/2016 | ............. A61N 1/375 |

OTHER PUBLICATIONS

International Search Report and Written Opinion in PCT/IB2018/052727, dated Aug. 3, 2018.

* cited by examiner

*Primary Examiner* — Christine H Matthews
*Assistant Examiner* — Joshua Daryl D Lannu
(74) *Attorney, Agent, or Firm* — Pilloff Passino & Cosenza LLP; Martin J. Cosenza

(57) ABSTRACT

An implantable prosthesis, including an implantable component including an implantable magnet assembly, wherein the magnet assembly includes a magnet plated with a metallic substance, the magnet assembly includes a housing made at least in part of a polymer, wherein at least a portion of the housing made out of the polymer is in direct contact with the metallic substance, and the implantable component is configured to be implanted in a human such that the housing is exposed to body fluids thereof.

31 Claims, 35 Drawing Sheets

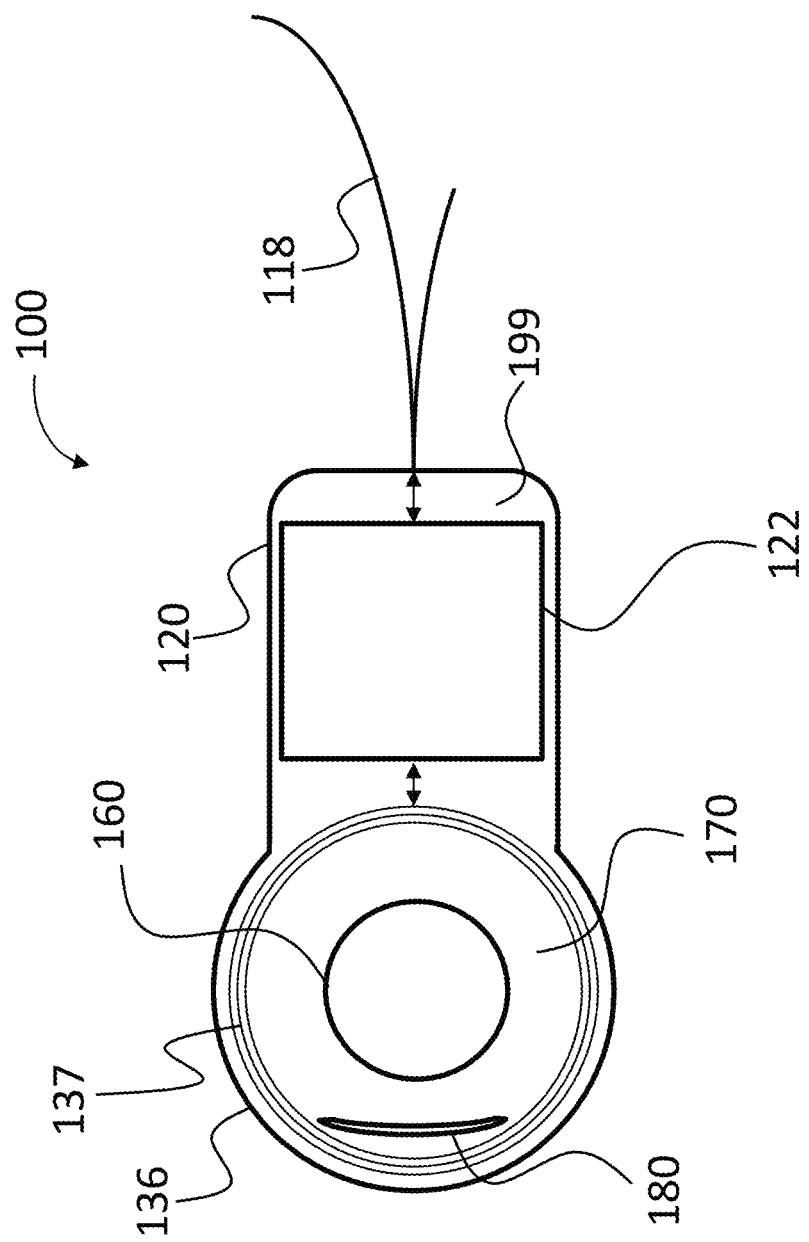

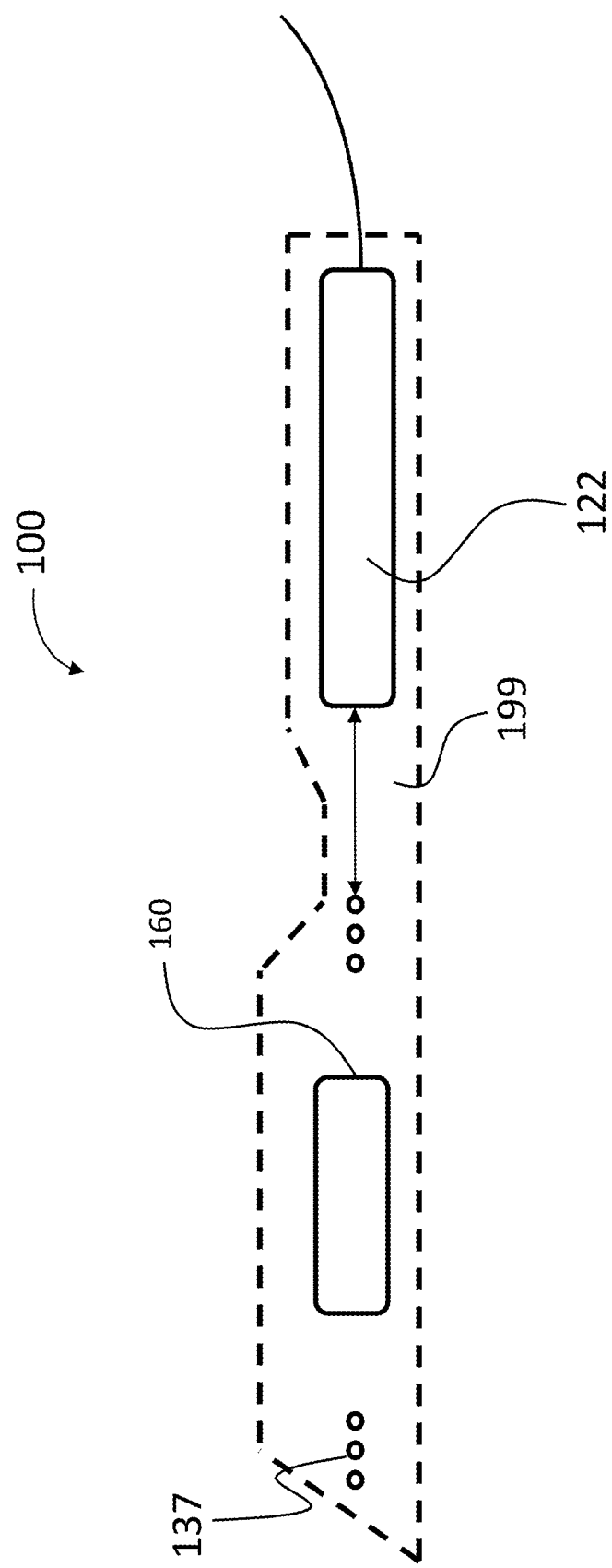

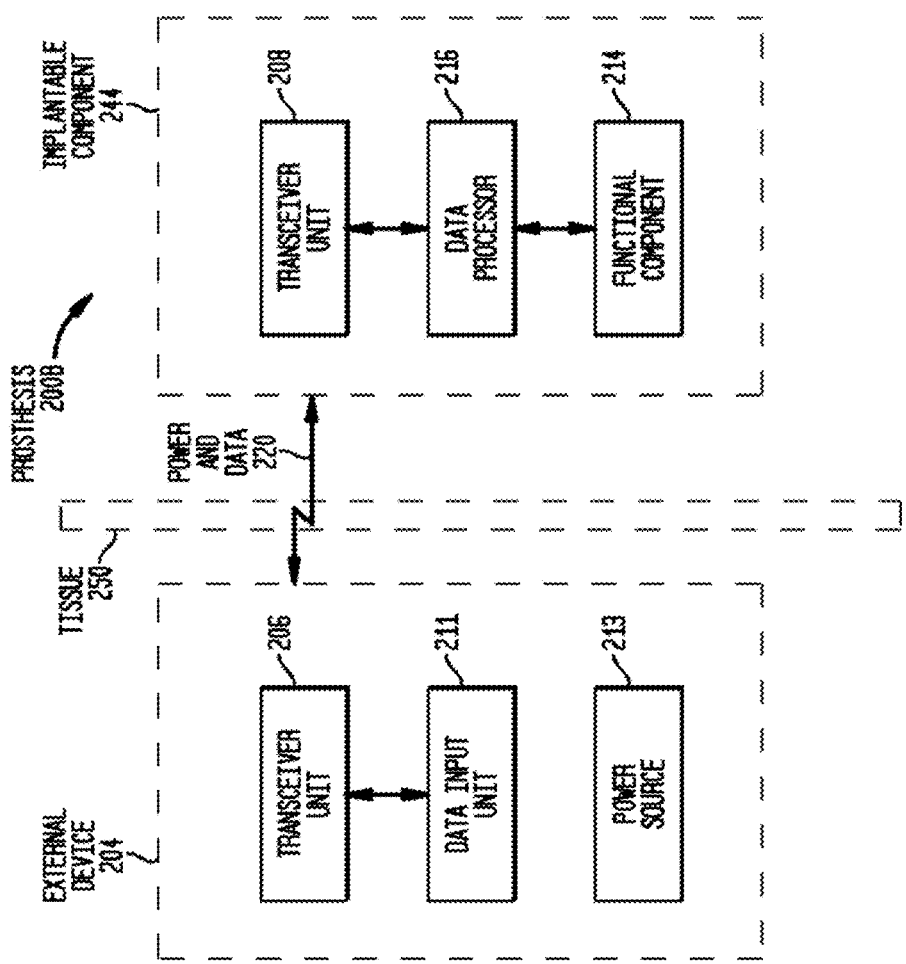

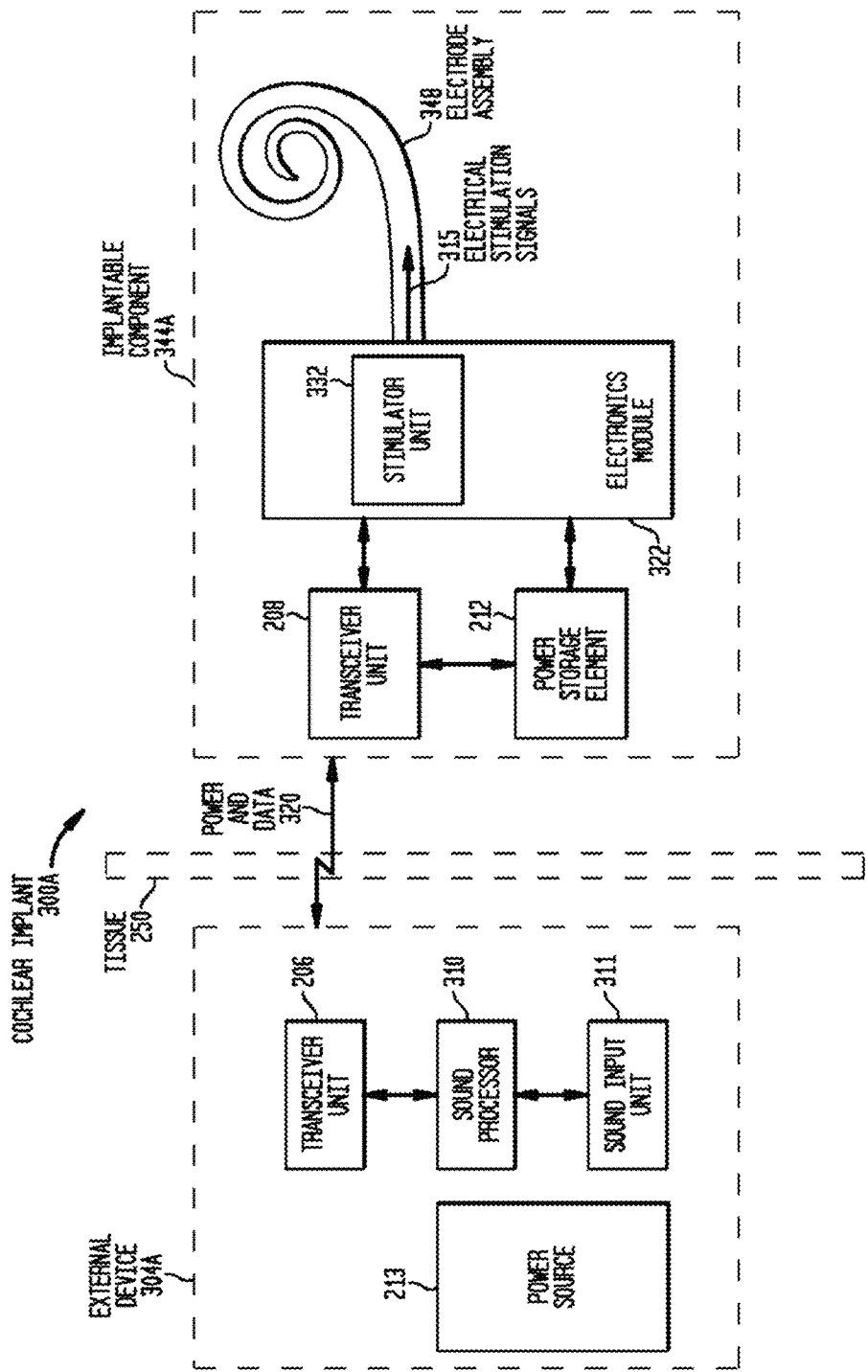

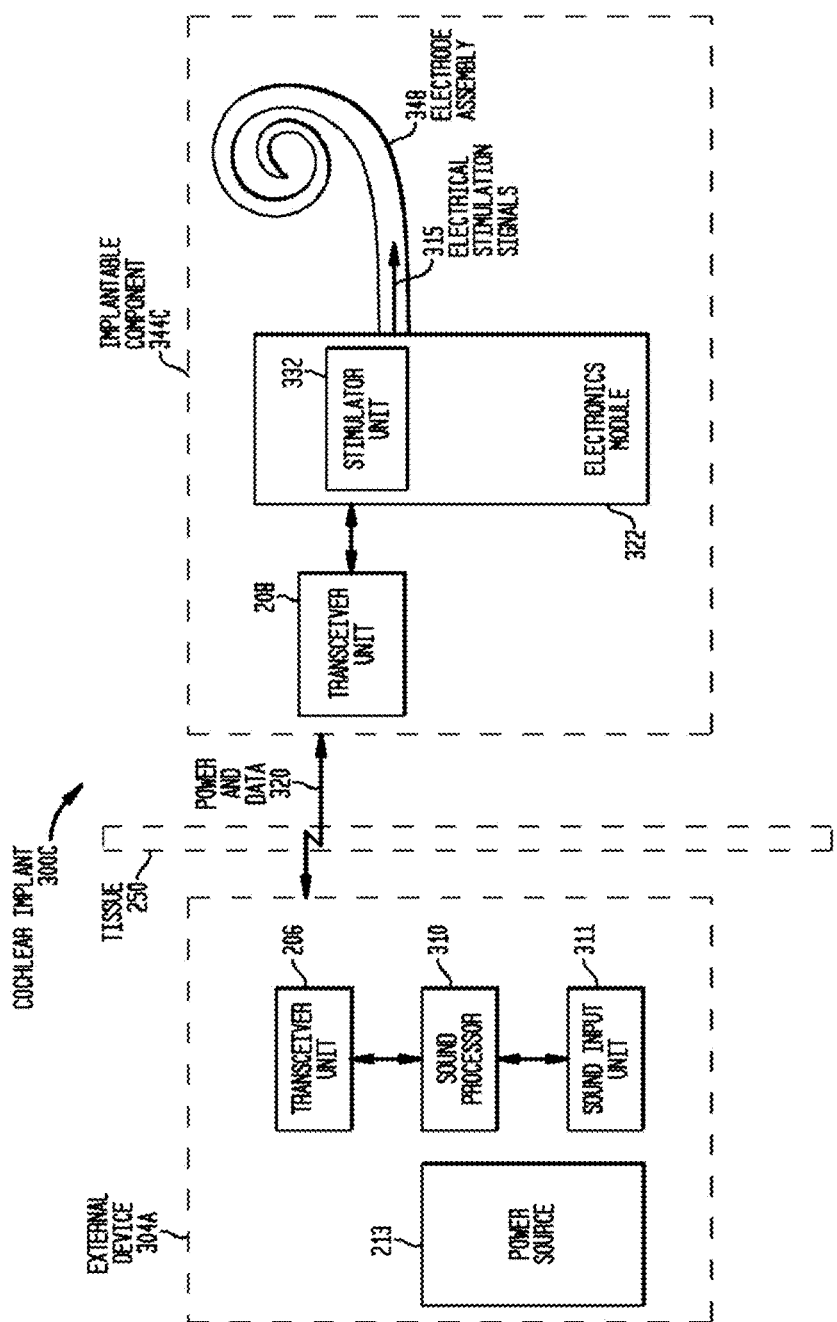

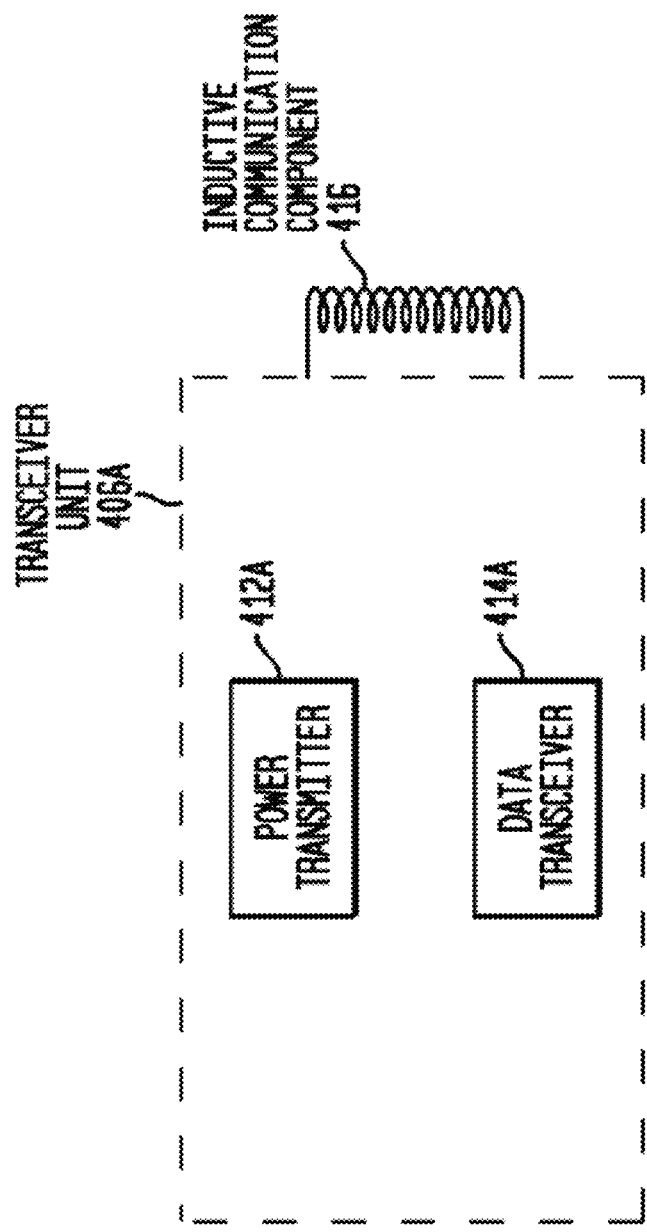

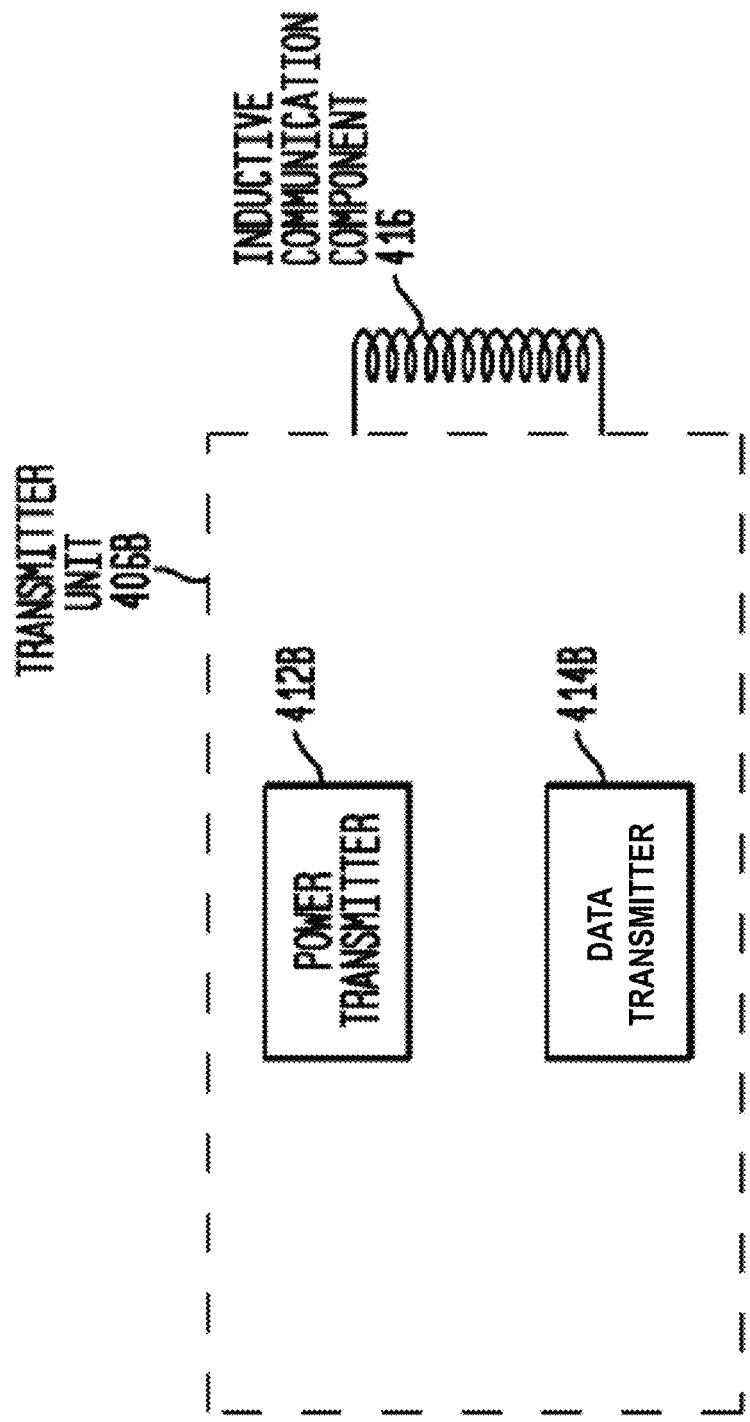

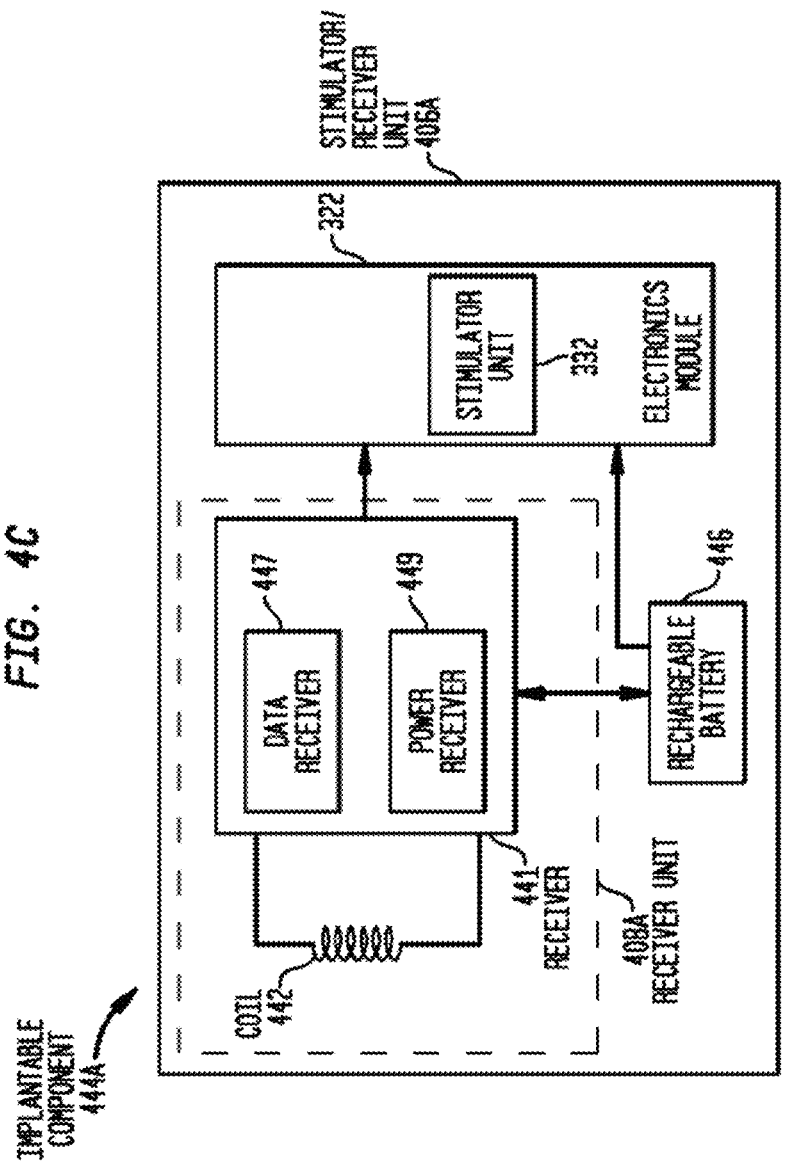

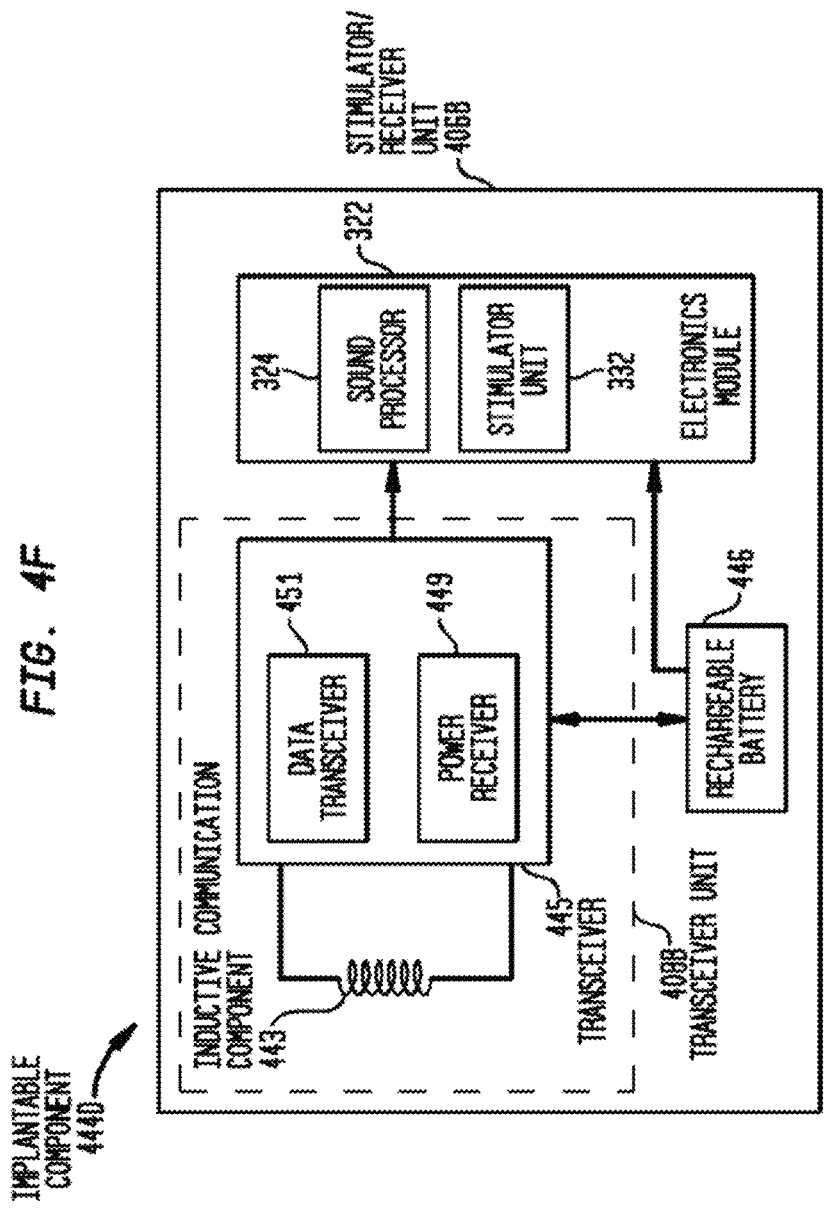

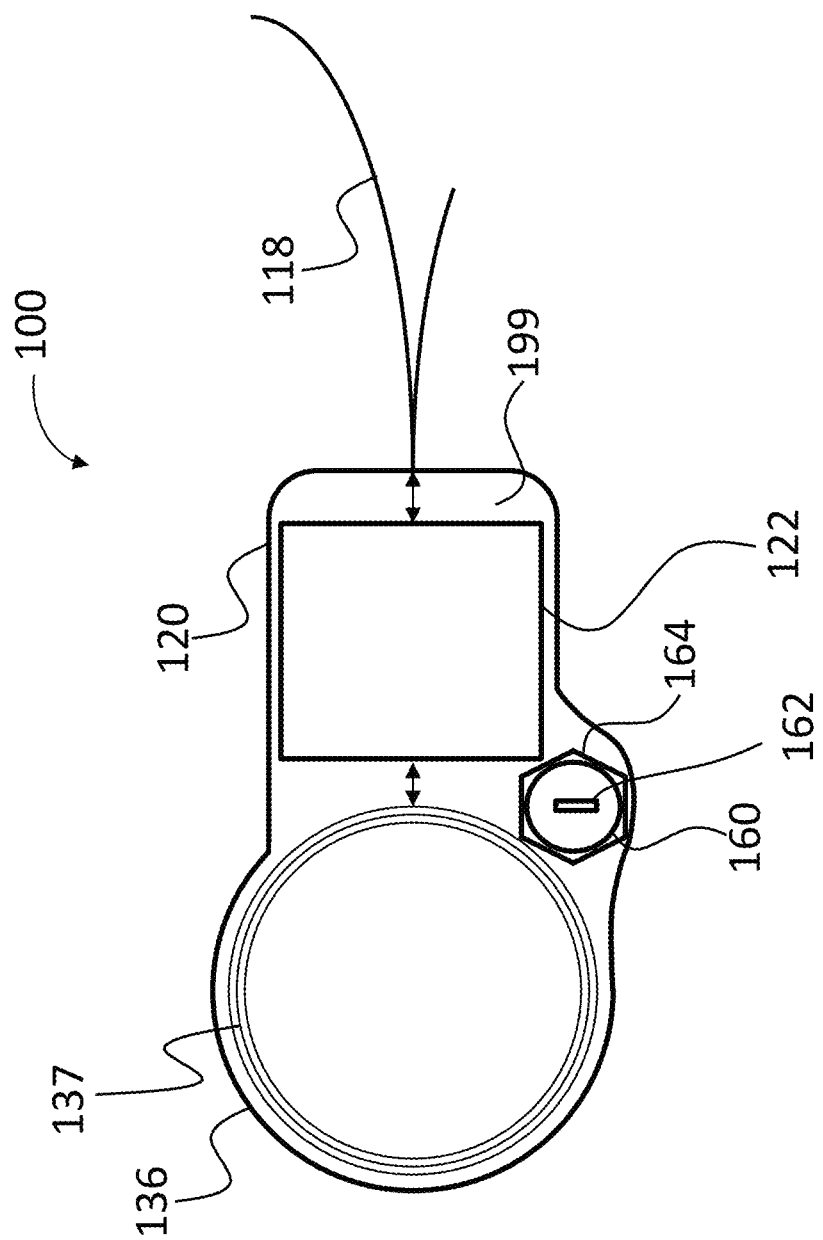

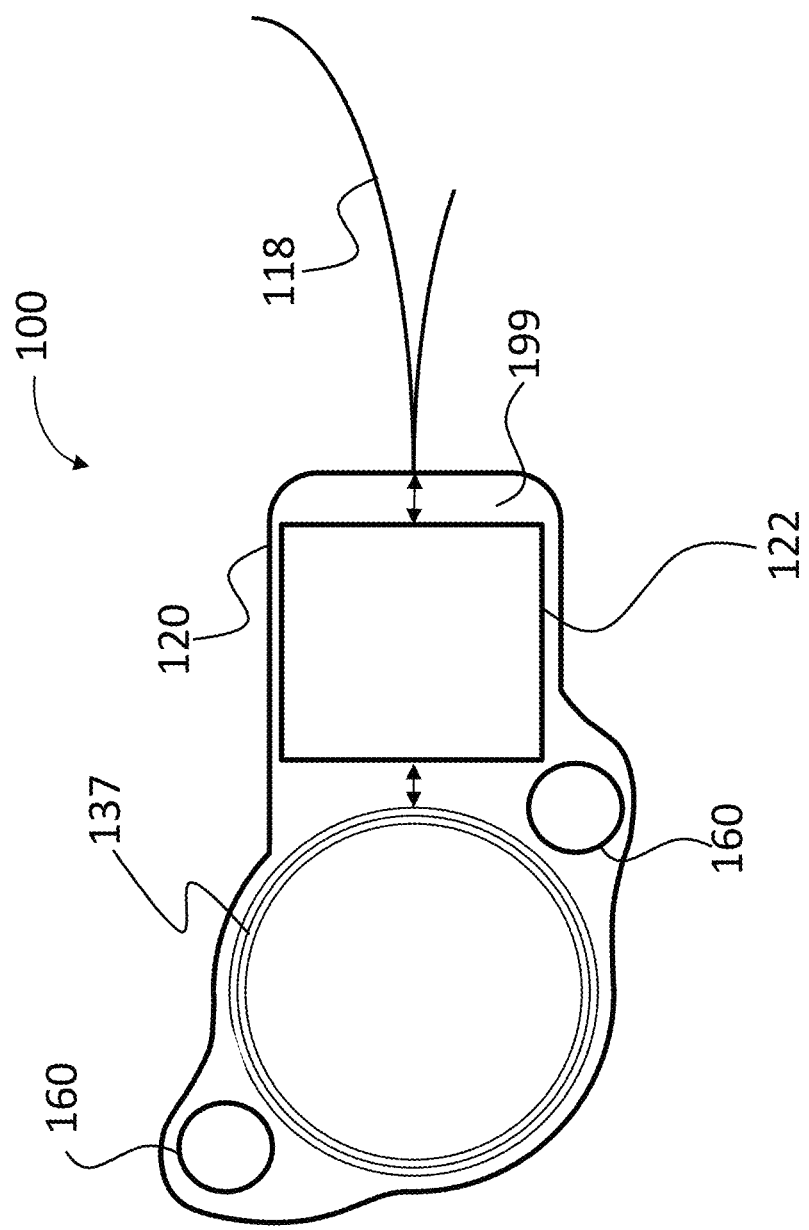

MAGNET SUPPORT OF AN IMPLANT

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses, commonly referred to as cochlear implants, convert a received sound into electrical stimulation. The electrical stimulation is applied to the cochlea, which results in the perception of the received sound. It is utilitarian to place an electrode array of the cochlear implant into the cochlea.

SUMMARY

In accordance with an exemplary embodiment, there is an implantable prosthesis, comprising an implantable component including an implantable magnet assembly, wherein the magnet assembly includes a magnet plated with a metallic substance, the magnet assembly includes a housing made at least in part of a polymer, wherein the magnet is located in the housing, wherein at least a portion of the housing made out of the polymer is in direct contact with the metallic substance, and the implantable component is configured to be implanted in a human such that the housing is exposed to body fluids thereof.

In accordance with another exemplary embodiment, there is an implantable prosthesis, comprising an implantable functional component including an implantable first housing and an implantable magnet assembly, the first housing having electronics located therein, wherein the magnet assembly includes a plated magnet located in a second housing, the second housing is established by structural components that are carbon or silicone chain based components, and the magnet assembly includes only one housing, the only one housing corresponding to the second housing.

In accordance with another exemplary embodiment, there is an implantable magnet assembly, comprising a magnet coated with a substance, the magnet being located in a housing, wherein the implantable magnet assembly is configured to be implanted in a human such that the housing is exposed to body fluids thereof, and the assembly is configured to protect the magnet from body fluids via a system that consists of the substance that coats the magnet and one or more non-metallic pliable components.

In accordance with another exemplary embodiment, there is a method, comprising establishing or breaking a magnetic attractive field between a first magnet of an external component of a prosthesis and a second magnet of an implanted component of the prosthesis, a portion of a magnetic path of the magnetic attractive field between the first magnet and the second magnet that extends through the recipient to the second magnet passing though at most only carbon based substances, silicon based substances, air, water based substances, and a metallic coating of the second magnet.

BRIEF DESCRIPTION OF THE DRAWINGS

Embodiments are described below with reference to the attached drawings, in which:

FIG. 1B is a top view of an exemplary hearing prosthesis in which at least some of the teachings detailed herein are applicable;

FIG. 1C is a side view of an exemplary hearing prosthesis in which at least some of the teachings detailed herein are applicable;

FIG. 2B is an alternate functional block diagram of a prosthesis, in accordance with embodiments of the present invention;

FIG. 3A is a functional block diagram of a cochlear implant, in accordance with embodiments of the present invention;

FIG. 3C is yet another alternate functional block diagram of a cochlear implant, in accordance with embodiments of the present invention;

FIG. 4A is a simplified schematic diagram of a transceiver unit of an external device in accordance with embodiments of the present invention;

FIG. 4B is a simplified schematic diagram of a transmitter unit of an external device in accordance with embodiments of the present invention;

FIG. 4C is a simplified schematic diagram of a stimulator/receiver unit including a data receiver of an implantable device in accordance with embodiments of the present invention;

FIG. 4F is a simplified schematic diagram of a stimulator/receiver unit including a data transceiver and a communication component configured to vary the effective coil area of an implantable device in accordance with embodiments of the present invention;

FIGS. 7A-9 represent exemplary conceptual schematics of various exemplary embodiments of some implantable components according to the teachings detailed herein;

DETAILED DESCRIPTION

Exemplary embodiments will be described in terms of a cochlear implant. That said, it is noted that the teachings detailed herein and/or variations thereof can be utilized with other types of hearing prostheses, such as by way of example, bone conduction devices, DACI/DACS/middle ear implants, etc. Still further, it is noted that the teachings detailed herein and/or variations thereof can be utilized with other types of prostheses, such as pacemakers, muscle stimulators, etc. In some instances, the teachings detailed herein and/or variations thereof are applicable to any type of implanted component (herein referred to as a medical device) having a magnet that is implantable in a recipient.

Figure 1A:
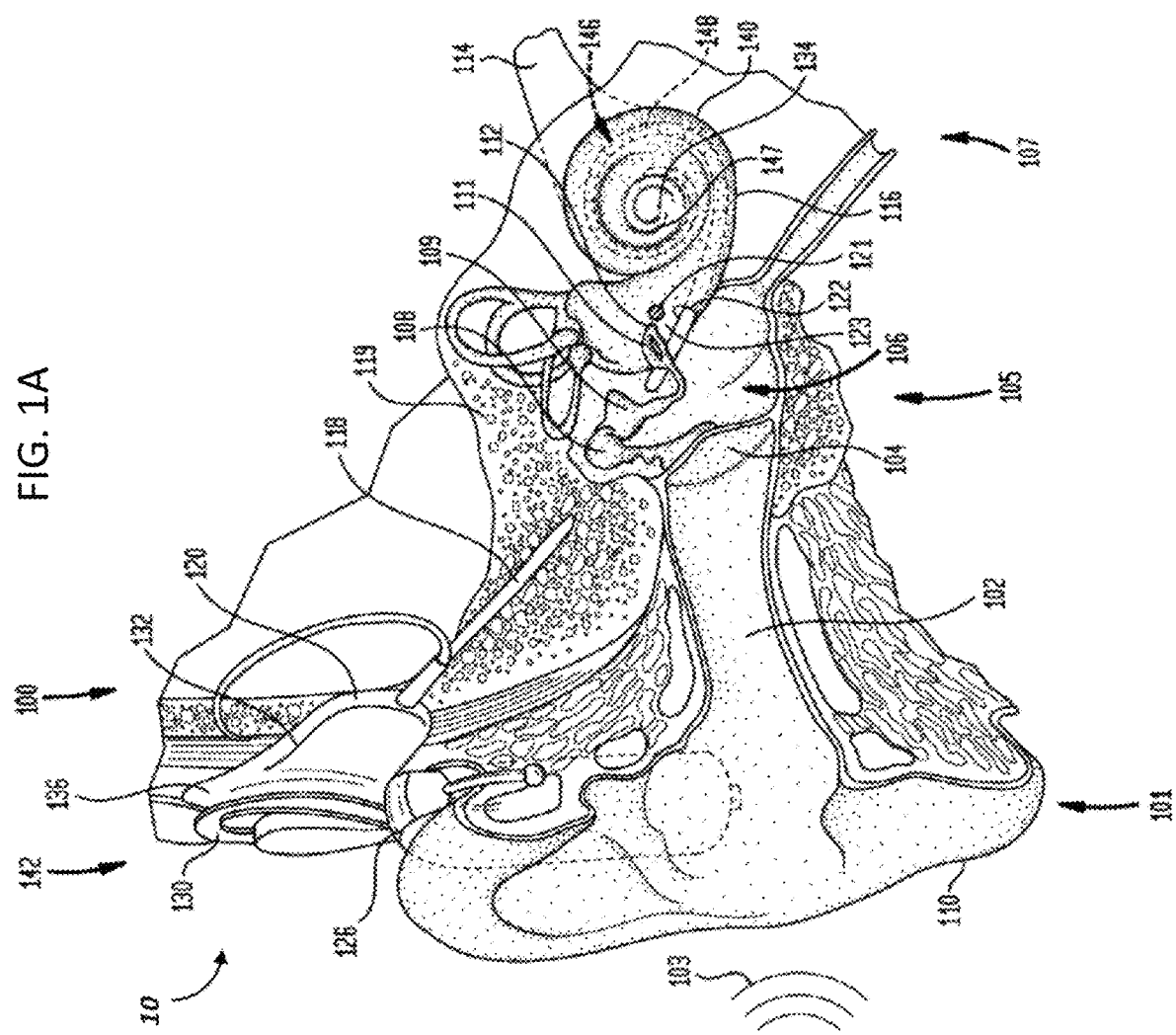
FIG. 1A is a perspective view of an exemplary hearing prosthesis in which at least some of the teachings detailed herein are applicable.

FIG. 1A is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.). Additionally, it is noted that the teachings detailed herein are also applicable to other types of hearing prostheses, such as by way of example only and not by way of limitation, bone conduction devices, direct acoustic cochlear stimulators, middle ear implants, etc. Indeed, it is noted that the teachings detailed herein are also applicable to so-called hybrid devices. In an exemplary embodiment, these hybrid devices apply both electrical stimulation and acoustic stimulation to the recipient. Any type of hearing prosthesis to which the teachings detailed herein and/or variations thereof that can have utility can be used in some embodiments of the teachings detailed herein.

In view of the above, it is to be understood that at least some embodiments detailed herein and/or variations thereof are directed towards a body-worn sensory supplement medical device (e.g., the hearing prosthesis of FIG. 1A, which supplements the hearing sense, even in instances where all natural hearing capabilities have been lost). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities remaining and to recipients having no natural vision capabilities remaining). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired.

The recipient has an outer ear 101, a middle ear 105, and an inner ear 107. Components of outer ear 101, middle ear 105, and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1A with an external device 142, that is part of system 10 (along with cochlear implant 100), which, as described below, is configured to provide power to the cochlear implant, and where the implanted cochlear implant includes a battery, that is recharged by the power provided from the external device 142.

In the illustrative arrangement of FIG. 1A, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1A, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1A is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil assembly 137. Internal coil assembly 137 typically includes a wire antenna coil comprised of multiple turns of electrically insulated single-strand or multi-strand platinum or gold wire, as will be described in greater detail below.

Cochlear implant 100 further comprises a main implantable component 120 and an elongate electrode assembly 118. Collectively, the coil assembly 137, the main implantable component 120, and the electrode assembly 118 correspond to the implantable component of the system 10.

In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone or via internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown in FIG. 1A) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123, or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

FIG. 1B depicts an exemplary high-level diagram of the implantable component 100 of the system 10, looking downward from outside the skull towards the skull. As can be seen, implantable component 100 includes a magnet 160 that is surrounded by a coil 137 that is in two-way communication (although in some instances, the communication is one-way) with a stimulator unit 122, which in turn is in communication with the electrode assembly 118.

Still with reference to FIG. 1B, it is noted that the stimulator unit 122, and the magnet apparatus 160 are located in a housing made of an elastomeric material 199, such as by way of example only and not by way of limitation, silicone. Hereinafter, the elastomeric material 199 of the housing will be often referred to as silicone. However, it is noted that any reference to silicone herein also corresponds to a reference to any other type of component that will enable the teachings detailed herein and/or variations thereof, such as, by way of example and not by way of limitation only, bio-compatible rubber, etc.

As can be seen in FIG. 1B, the housing made of elastomeric material 199 includes a slit (or a slot, in some alternate embodiments) 180 (not shown in FIG. 1C, as, in some instances, the slit is not utilized). In some variations, the slit 180 has utilitarian value in that it can enable insertion and/or removal of the magnet apparatus 160 from the housing made of elastomeric material 199. It is noted that any disclose herein of a slit also corresponds to a disclosure of a slot, and visa-versa.

It is noted that magnet apparatus 160 is presented in a conceptual manner. In this regard, it is noted that in at least some instances, the magnet apparatus 160 is an assembly that includes a magnet surrounded by a biocompatible coating. Still further by way of example, magnet apparatus 160 is an assembly where the magnet is located within a container having interior dimensions generally corresponding to the exterior dimensions of the magnet. This container can be hermetically sealed, thus isolating the magnet in the container from body fluids of the recipient that penetrate the housing (the same principle of operation occurs with respect to the aforementioned coated magnet). In an exemplary embodiment, this container permits the magnet to revolve or otherwise move relative to the container. Additional details of the container will be described below. In this regard, it is noted that while sometimes the term magnet is used as shorthand for the phrase magnet apparatus, and thus any disclosure herein with respect to a magnet also corresponds to a disclosure of a magnet apparatus according to the aforementioned embodiments and/or variations thereof and/or any other configuration that can have utilitarian value according to the teachings detailed herein.

Briefly, it is noted that there is utilitarian value with respect to enabling the magnet to revolve within the container or otherwise move. In this regard, in an exemplary embodiment, when the magnet is introduced to an external magnetic field, such as in an MRI machine, the magnet can revolve or otherwise move to substantially align with the external magnetic field. In an exemplary embodiment, this alignment can reduce or otherwise eliminate the torque on the magnet, thus reducing discomfort and/or reducing the likelihood that the implantable component will be moved during the MRI procedure (potentially requiring surgery to place the implantable component at its intended location) and thus reduce and/or eliminate the demagnetization of the magnet.

Element 136 can be considered a housing of the coil, in that it is part of the housing 199.

With reference now to FIG. 1C, it is noted that the outlines of the housing made from elastomeric material 199 are presented in dashed line format for ease of discussion. In an exemplary embodiment, silicone or some other elastomeric material fills the interior within the dashed line, other than the other components of the implantable device (e.g., plates, magnet, stimulator, etc.). That said, in an alternative embodiment, silicone or some other elastomeric material substantially fills the interior within the dashed lines other than the components of the implantable device (e.g., there can be pockets within the dashed line in which no components and no silicone are located).

It is noted that FIGS. 1B and 1C are conceptual FIGS. presented for purposes of discussion. Commercial embodiments corresponding to these FIGS. can be different from that depicted in the figures.

Figure 2A:
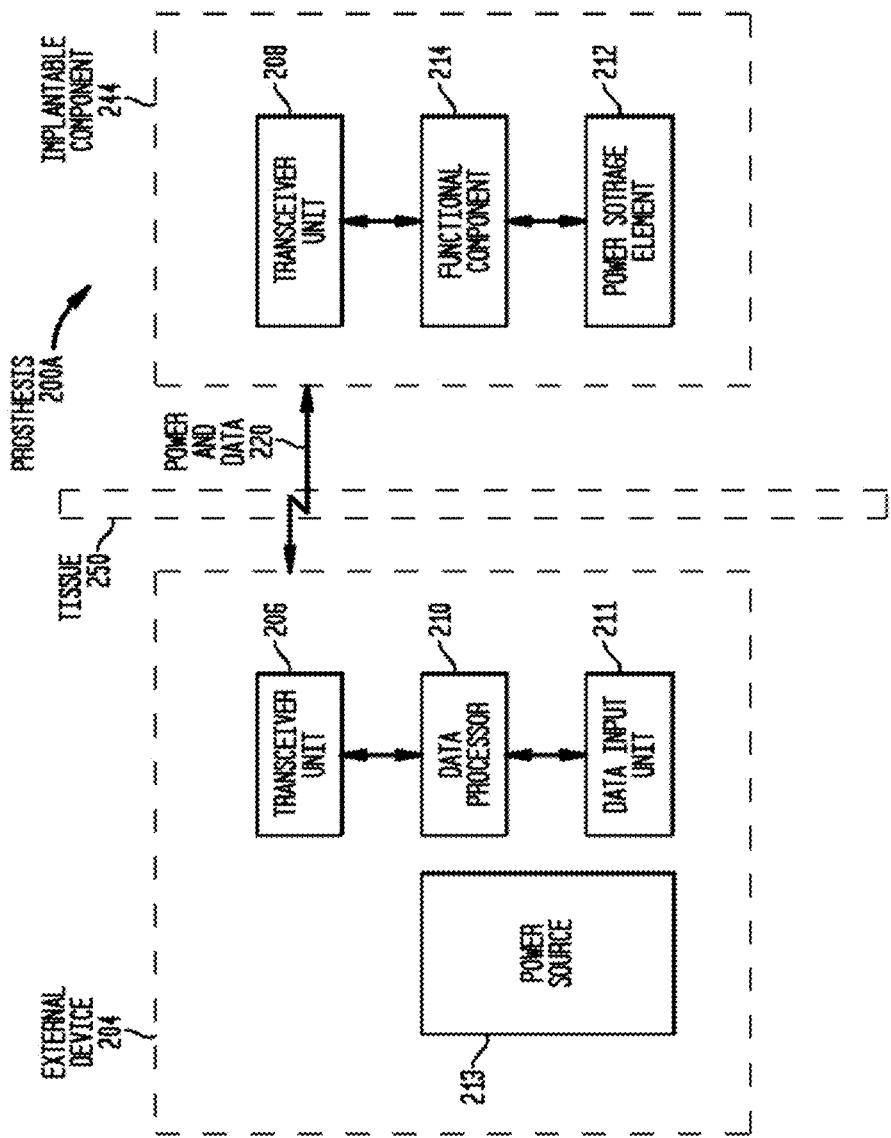
FIG. 2A is a functional block diagram of a prosthesis, in accordance with embodiments of the present invention.

FIG. 2A is a functional block diagram of a prosthesis 200A in accordance with embodiments of the present invention. Prosthesis 200A comprises an implantable component 244 configured to be implanted beneath a recipient's skin or other tissue 250 and an external device 204. For example, implantable component 244 may be implantable component 100 of FIG. 1A, and external device may be the external device 142 of FIG. 1A. Similar to the embodiments described above with reference to FIG. 1A, implantable component 244 comprises a transceiver unit 208 which receives data and power from external device 204. External device 204 transmits power and data 220 via transceiver unit 206 to transceiver unit 208 via a magnetic induction data link 220. As used herein, the term receiver refers to any device or component configured to receive power and/or data such as the receiving portion of a transceiver or a separate component for receiving. The details of transmission of power and data to transceiver unit 208 are provided below. With regard to transceivers, it is noted at this time that while embodiments of the present invention may utilize transceivers, separate receivers and/or transmitters may be utilized as appropriate. This will be apparent in view of the description below.

Implantable component 244 may comprises a power storage element 212 and a functional component 214. Power storage element 212 is configured to store power received by transceiver unit 208, and to distribute power, as needed, to the elements of implantable component 244. Power storage element 212 may comprise, for example, a rechargeable battery 212. An example of a functional component may be a stimulator unit 120 as shown in FIG. 1B.

In certain embodiments, implantable component 244 may comprise a single unit having all components of the implantable component 244 disposed in a common housing. In other embodiments, implantable component 244 comprises a combination of several separate units communicating via wire or wireless connections. For example, power storage element 212 may be a separate unit enclosed in a hermetically sealed housing. The implantable magnet apparatus and plates associated therewith may be attached to or otherwise be a part of any of these units, and more than one of these units can include the magnet apparatus and plates according to the teachings detailed herein and/or variations thereof.

In the embodiment depicted in FIG. 2A, external device 204 includes a data processor 210 that receives data from data input unit 211 and processes the received data. The processed data from data processor 210 is transmitted by transceiver unit 206 to transceiver unit 208. In an exemplary embodiment, data processor 210 may be a sound processor, such as the sound processor of FIG. 1A for the cochlear implant thereof, and data input unit 211 may be a microphone of the external device.

FIG. 2B presents an alternate embodiment of the prosthesis 200A of FIG. 2A, identified in FIG. 2B as prosthesis 200B. As may be seen from comparing FIG. 2A to FIG. 2B, the data processor can be located in the external device 204 or can be located in the implantable component 244. In some embodiments, both the external device 204 and the implantable component 244 can include a data processor.

As shown in FIGS. 2A and 2B, external device 204 can include a power source 213. Power from power source 213 can be transmitted by transceiver unit 206 to transceiver unit 208 to provide power to the implantable component 244, as will be described in more detail below.

While not shown in FIGS. 2A and 2B, external device 204 and/or implantable component 244 include respective inductive communication components. These inductive communication components can be connected to transceiver unit 206 and transceiver unit 208, permitting power and data 220 to be transferred between the two units via magnetic induction.

As used herein, an inductive communication component includes both standard induction coils and inductive communication components configured to vary their effective coil areas.

As noted above, prosthesis 200A of FIG. 2A may be a cochlear implant. In this regard, FIG. 3A provides additional details of an embodiment of FIG. 2A where prosthesis 200A is a cochlear implant. Specifically, FIG. 3A is a functional block diagram of a cochlear implant 300 in accordance with embodiments of the present invention.

It is noted that the components detailed in FIGS. 2A and 2B may be identical to the components detailed in FIG. 3A, and the components of 3A may be used in the embodiments depicted in FIGS. 2A and 2B.

Cochlear implant 300A comprises an implantable component 344A (e.g., implantable component 100 of FIG. 1) configured to be implanted beneath a recipient's skin or other tissue 250, and an external device 304A. External device 304A may be an external component such as external component 142 of FIG. 1.

Similar to the embodiments described above with reference to FIGS. 2A and 2B, implantable component 344A comprises a transceiver unit 208 (which may be the same transceiver unit used in FIGS. 2A and 2B) which receives data and power from external device 304A. External device 304A transmits data and/or power 320 to transceiver unit 208 via a magnetic induction data link. This can be done while charging module 202.

Implantable component 344A also comprises a power storage element 212, electronics module 322 (which may include components such as sound processor 126 and/or may include a stimulator unit 322 corresponding to stimulator unit 122 of FIG. 1B) and an electrode assembly 348 (which may include an array of electrode contacts 148 of FIG. 1A). Power storage element 212 is configured to store power received by transceiver unit 208, and to distribute power, as needed, to the elements of implantable component 344A.

As shown, electronics module 322 includes a stimulator unit 332. Electronics module 322 can also include one or more other functional components used to generate or control delivery of electrical stimulation signals 315 to the recipient. As described above with respect to FIG. 1A, electrode assembly 348 is inserted into the recipient's cochlea and is configured to deliver electrical stimulation signals 315 generated by stimulator unit 332 to the cochlea.

In the embodiment depicted in FIG. 3A, the external device 304A includes a sound processor 310 configured to convert sound signals received from sound input unit 311 (e.g., a microphone, an electrical input for an FM hearing system, etc.) into data signals. In an exemplary embodiment, the sound processor 310 corresponds to data processor 210 of FIG. 2A.

Figure 3B:
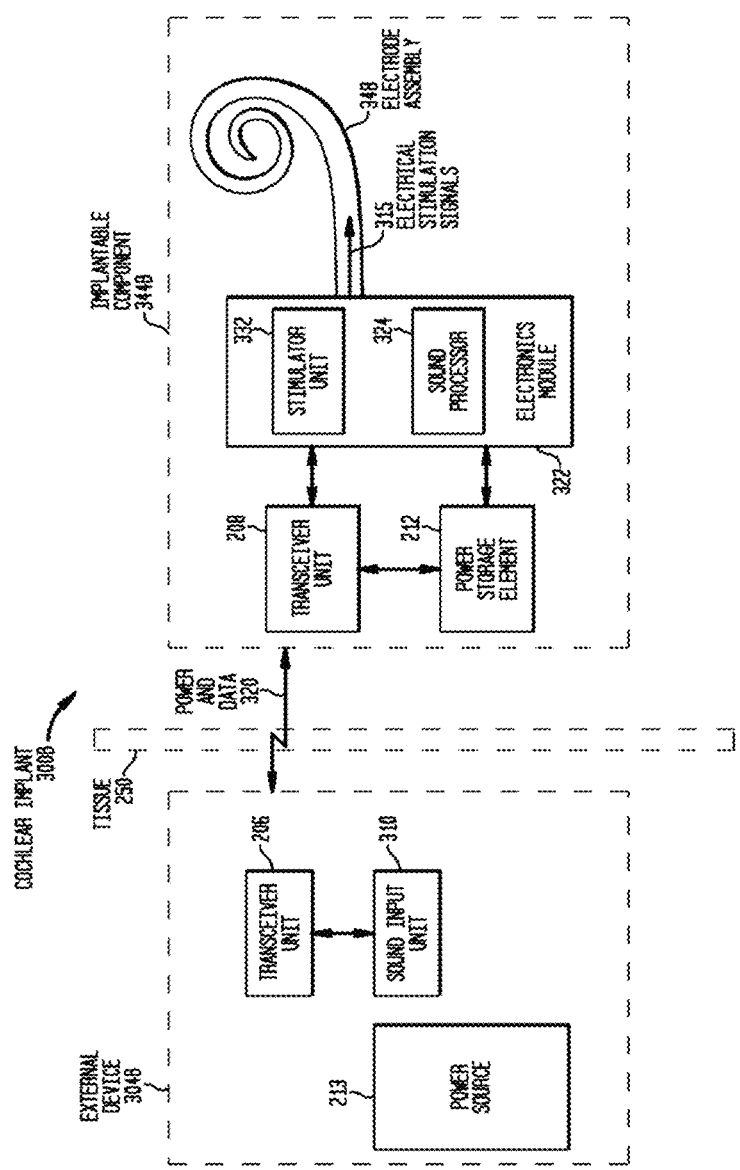
FIG. 3B is an alternate functional block diagram of a cochlear implant, in accordance with embodiments of the present invention.

FIG. 3B presents an alternate embodiment of a cochlear implant 300B. The elements of cochlear implant 300B correspond to the elements of cochlear implant 300A, except that external device 304B does not include sound processor 310. Instead, the implantable component 344B includes a sound processor 324, which may correspond to sound processor 310 of FIG. 3A.

As will be described in more detail below, while not shown in the figures, external device 304A/304B and/or implantable component 344A/344B include respective inductive communication components.

FIGS. 3A and 3B illustrate that external device 304A/304B can include a power source 213, which may be the same as power source 213 depicted in FIG. 2A. Power from power source 213 can be transmitted by transceiver unit 306 to transceiver unit 308 to provide power to the implantable component 344A/344B, as will be detailed below. FIGS. 3A and 3B further detail that the implantable component 344A/344B can include a power storage element 212 that stores power received by the implantable component 344 from power source 213. Power storage element 212 may be the same as power storage element 212 of FIG. 2A.

In contrast to the embodiments of FIGS. 3A and 3B, as depicted in FIG. 3C, an embodiment of the present invention of a cochlear implant 300C includes an implantable component 344C that does not include a power storage element 212. In the embodiment of FIG. 3C, sufficient power is supplied by external device 304A/304B in real time to power implantable component 344C without storing power in a power storage element. In FIG. 3C, all of the elements are the same as FIG. 3A except for the absence of power storage element 212.

Some of the components of FIGS. 3A-3C will now be described in greater detail.

FIG. 4A is a simplified schematic diagram of a transceiver unit 406A in accordance with an embodiment of the present invention. An exemplary transceiver unit 406A may correspond to transceiver unit 206 of FIGS. 2A-3C. As shown, transceiver unit 406A includes a power transmitter 412A, a data transceiver 414A and an inductive communication component 416.

In an exemplary embodiment, as will be described in more detail below, inductive communication component 416 comprises one or more wire antenna coils (depending on the embodiment) comprised of multiple turns of electrically insulated single-strand or multi-strand platinum or gold wire (thus corresponding to coil 137 of FIG. 1B). Power transmitter 412A comprises circuit components that inductively transmit power from a power source, such as power source 213, via an inductive communication component 416 to implantable component 344A/B/C (FIGS. 3A-3C). Data transceiver 414A comprises circuit components that cooperate to output data for transmission to implantable component 344A/B/C (FIGS. 3A-3C). Transceiver unit 406A can receive inductively transmitted data from one or more other components of cochlear implant 300A/B/C, such as telemetry or the like from implantable component 344A (FIG. 3A).

Transceiver unit 406A can be included in a device that includes any number of components which transmit data to implantable component 334A/B/C. For example, the transceiver unit 406A may be included in a behind-the-ear (BTE) device having one or more of a microphone or sound processor therein, an in-the-ear device, etc.

FIG. 4B depicts a transmitter unit 406B, which is identical to transceiver unit 406A, except that it includes a power transmitter 412B and a data transmitter 414B.

It is noted that for ease of description, power transmitter 412A and data transceiver 414A/data transmitter 414B are shown separate. However, it should be appreciated that in certain embodiments, at least some of the components of the two devices may be combined into a single device.

FIG. 4C is a simplified schematic diagram of one embodiment of an implantable component 444A that corresponds to implantable component 344A of FIG. 3A, except that transceiver unit 208 is a receiver unit. In this regard, implantable component 444A comprises a receiver unit 408A, a power storage element, shown as rechargeable battery 446, and electronics module 322, corresponding to electronics module 322 of FIG. 3A. Receiver unit 408A includes an inductance coil 442 connected to receiver 441. Receiver 441 comprises circuit components which receive, via an inductive communication component corresponding to an inductance coil 442, inductively transmitted data and power from other components of cochlear implant 300A/B/C, such as from external device 304A/B. The components for receiving data and power are shown in FIG. 4C as data receiver 447 and power receiver 449. For ease of description, data receiver 447 and power receiver 449 are shown separate. However, it should be appreciated that in certain embodiments, at least some of the components of these receivers may be combined into one component.

In the illustrative embodiments of the present invention, receiver unit 408A and transceiver unit 406A (or transmitter unit 406B) establish a transcutaneous communication link over which data and power is transferred from transceiver unit 406A (or transmitter unit 406B), to implantable component 444A. As shown, the transcutaneous communication link comprises a magnetic induction link formed by an inductance communication component system that includes inductive communication component 416 and coil 442.

The transcutaneous communication link established by receiver unit 408A and transceiver unit 406A (or whatever other viable component can so establish such a link), in an exemplary embodiment, may use time interleaving of power and data on a single radio frequency (RF) channel or band to transmit the power and data to implantable component 444A. A method of time interleaving power according to an exemplary embodiment uses successive time frames, each having a time length and each divided into two or more time slots. Within each frame, one or more time slots are allocated to power, while one or more time slots are allocated to data. In an exemplary embodiment, the data modulates the RF carrier or signal containing power. In an exemplary embodiment, transceiver unit 406A and transmitter unit 406B are configured to transmit data and power, respectively, to an implantable component, such as implantable component 344A, within their allocated time slots within each frame.

The power received by receiver unit 408A can be provided to rechargeable battery 446 for storage. The power received by receiver unit 408A can also be provided for distribution, as desired, to elements of implantable component 444A. As shown, electronics module 322 includes stimulator unit 332, which in an exemplary embodiment corresponds to stimulator unit 322 of FIGS. 3A-3C, and can also include one or more other functional components used to generate or control delivery of electrical stimulation signals to the recipient.

In an embodiment, implantable component 444A comprises a receiver unit 408A, rechargeable battery 446 and electronics module 322 integrated in a single implantable housing, referred to as stimulator/receiver unit 406A. It would be appreciated that in alternative embodiments, implantable component 344 may comprise a combination of several separate units communicating via wire or wireless connections.

Figure 4D:
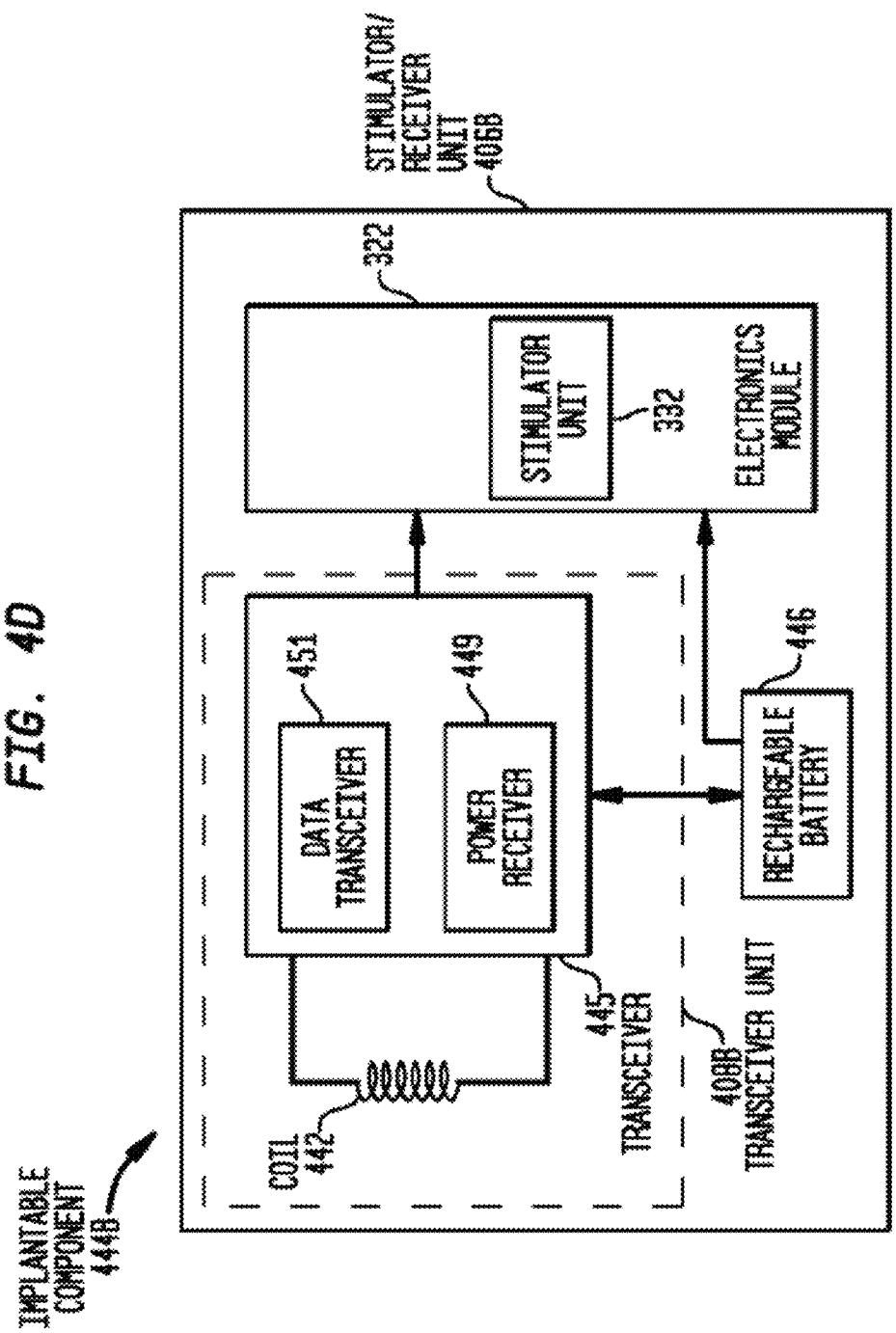
FIG. 4D is a simplified schematic diagram of a stimulator/receiver unit including a data transceiver of an implantable device in accordance with embodiments of the present invention.

FIG. 4D is a simplified schematic diagram of an alternate embodiment of an implantable component 444B. Implantable component 444B is identical to implantable component 444A of FIG. 4C, except that instead of receiver unit 408A, it includes transceiver unit 408B. Transceiver unit 408B includes transceiver 445 (as opposed to receiver 441 in FIG. 4C). Transceiver unit 445 includes data transceiver 451 (as opposed to data receiver 447 in FIG. 4C).

Figure 4E:
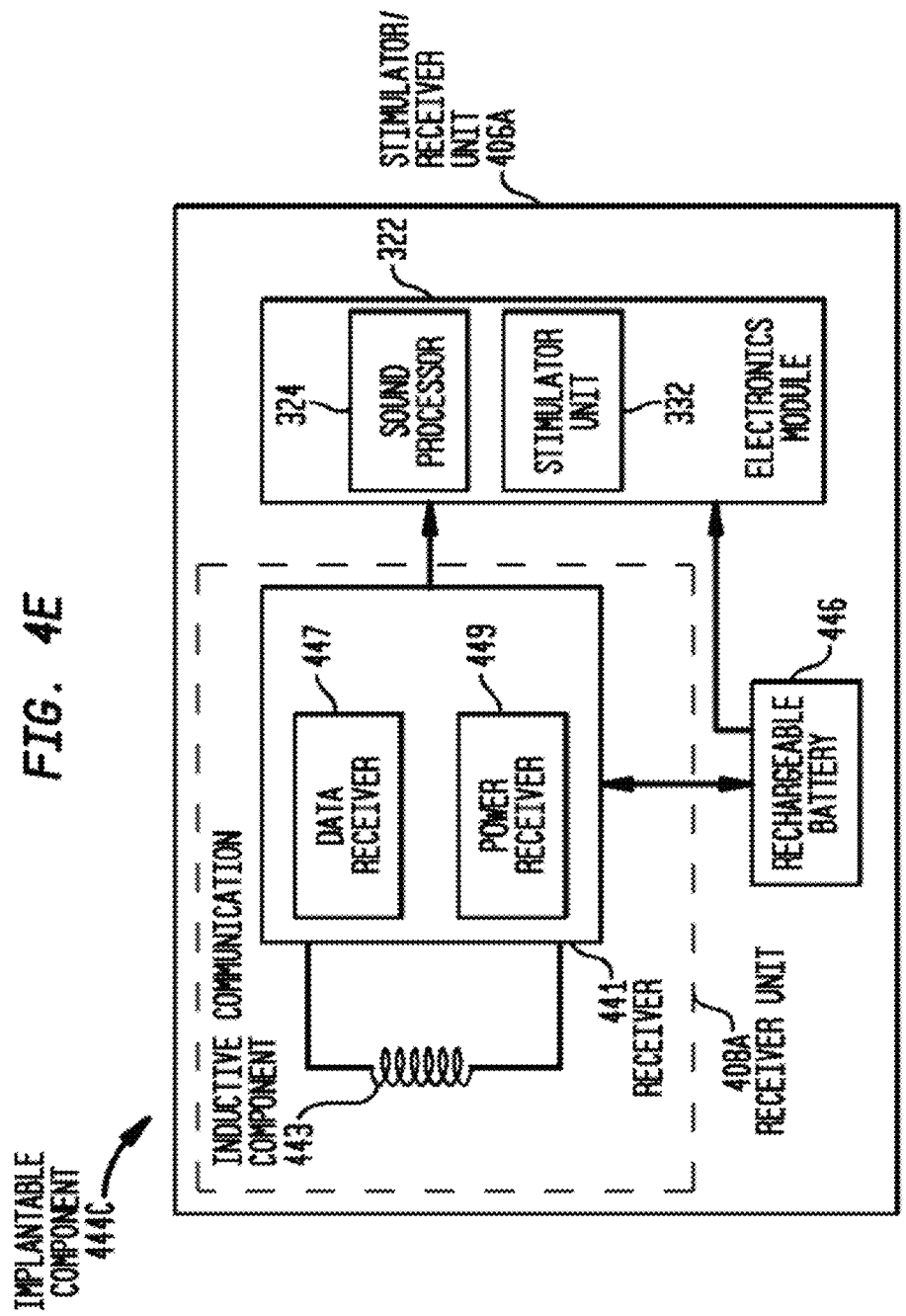
FIG. 4E is a simplified schematic diagram of a stimulator/receiver unit including a data receiver and a communication component configured to vary the effective coil area of an implantable device in accordance with embodiments of the present invention.

FIGS. 4E and 4F depict alternate embodiments of the implantable components 444A and 444B depicted in FIGS. 4C and 4D, respectively. In FIGS. 4E and 4F, instead of coil 442, implantable components 444C and 444D (FIGS. 4E and 4F, respectively) include inductive communication component 443. Inductive communication component 443 is configured to vary the effective coil area of the component, and may be used in cochlear implants where the exterior device 304A/B does not include a communication component configured to vary the effective coil area (i.e., the exterior device utilizes a standard inductance coil). In other respects, the implantable components 444C and 444D are substantially the same as implantable components 444A and 444B. Note that in the embodiments depicted in FIGS. 4E and 4F, the implantable components 444C and 444D are depicted as including a sound processor 342. In other embodiments, the implantable components 444C and 444D may not include a sound processor 342.

Figure 5:
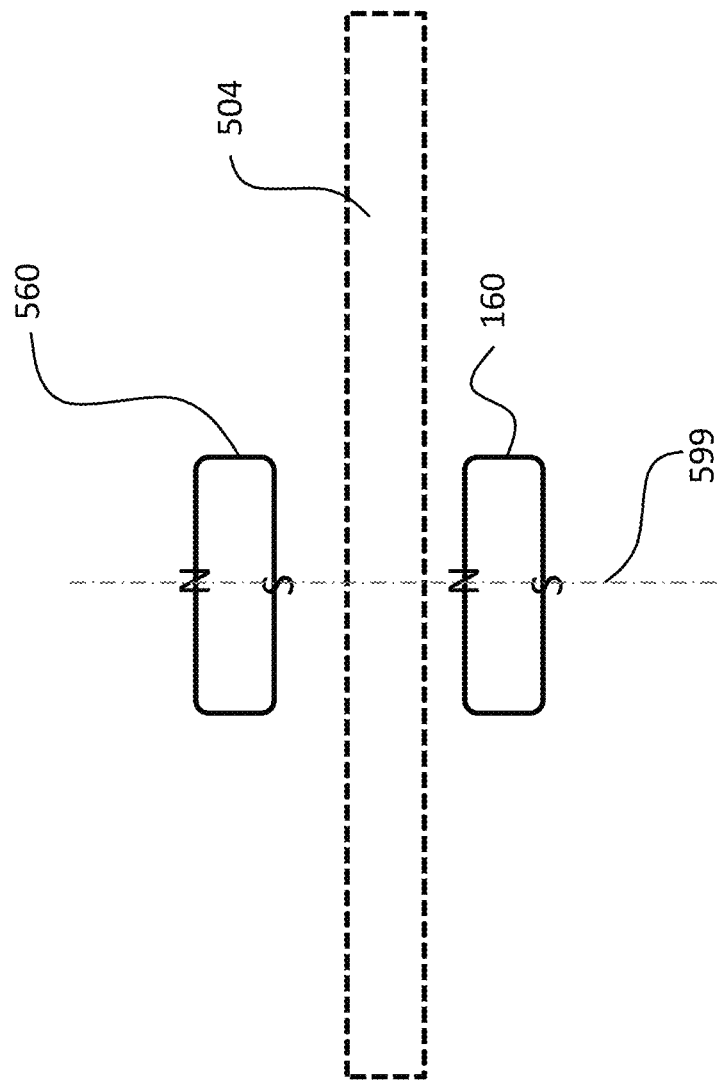
FIG. 5 is an exemplary conceptual schematic of a magnet system arrangement according to an exemplary embodiment.

FIG. 5 represents a high level conceptual exemplary magnetic coupling arrangement according to an exemplary embodiment. Specifically, FIG. 5 presents the magnet apparatus 160 of the implantable component 100 having a longitudinal axis 599 aligned with the magnet 560 of the external device 142, along with a functional representation of the tissue 504 of the recipient located between the two components. All other components of the external device and implantable component are not shown for purposes of clarity. As can be seen, the magnet apparatus 160 has a north-south polar axis aligned with the longitudinal axis 599, and magnet apparatus 560 also has a north-south polar axis aligned with the longitudinal axis of that magnet apparatus. In the exemplary embodiment, owing to the arrangements of the magnets, the resulting magnetic field aligns the magnets such that the longitudinal axes of the magnets are aligned. In an exemplary embodiment, because the various coils of the devices are aligned with the various longitudinal axes of the magnets, the alignment of the magnets aligns the coils.

Figure 6:
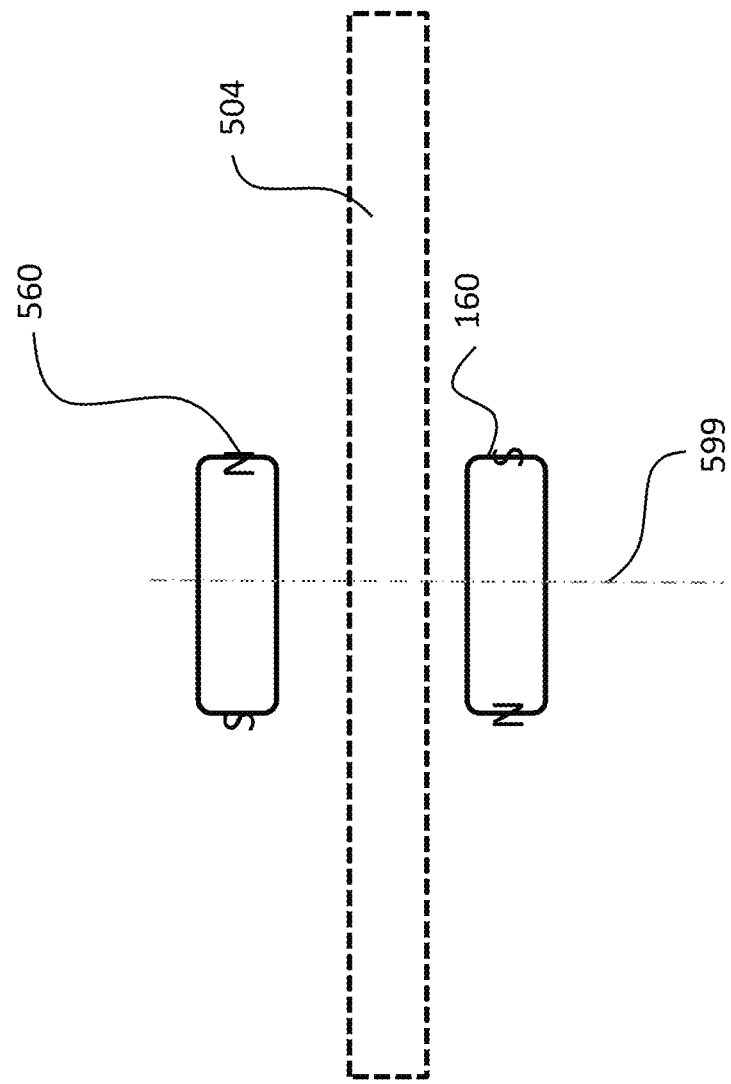
FIG. 6 is another exemplary conceptual schematic of a magnet system arrangement according to an exemplary embodiment.

FIG. 6 presents an alternative embodiment, where the magnet apparatus 160 of the implantable component 100 has a north-south axis aligned with the lateral axis of the magnet apparatus, as can be seen. In this exemplary embodiment, the magnet 560 also has a north-south axis also aligned with the lateral axis of that magnet. This arrangement is known as "in-plane" polarization.

As can be inferred from FIGS. 1B and 1C, the magnet apparatus of the implantable component 100 is a disk magnet apparatus/has the form of a short cylinder. The magnet of the external device 142 can also have such a form. That said, in an alternative embodiment, the magnets can have another configuration (e.g., a plate magnet, a bar magnet, etc.). Moreover, in an alternative embodiment, two or more magnets can be used in the implantable device and/or in the external device. The magnets could be located outboard of the coil. Any arrangement of magnet(s) of any configuration that can have utilitarian value according to the teachings detailed herein and/or variations thereof can be utilized in at least some embodiments.

Figure 7A:
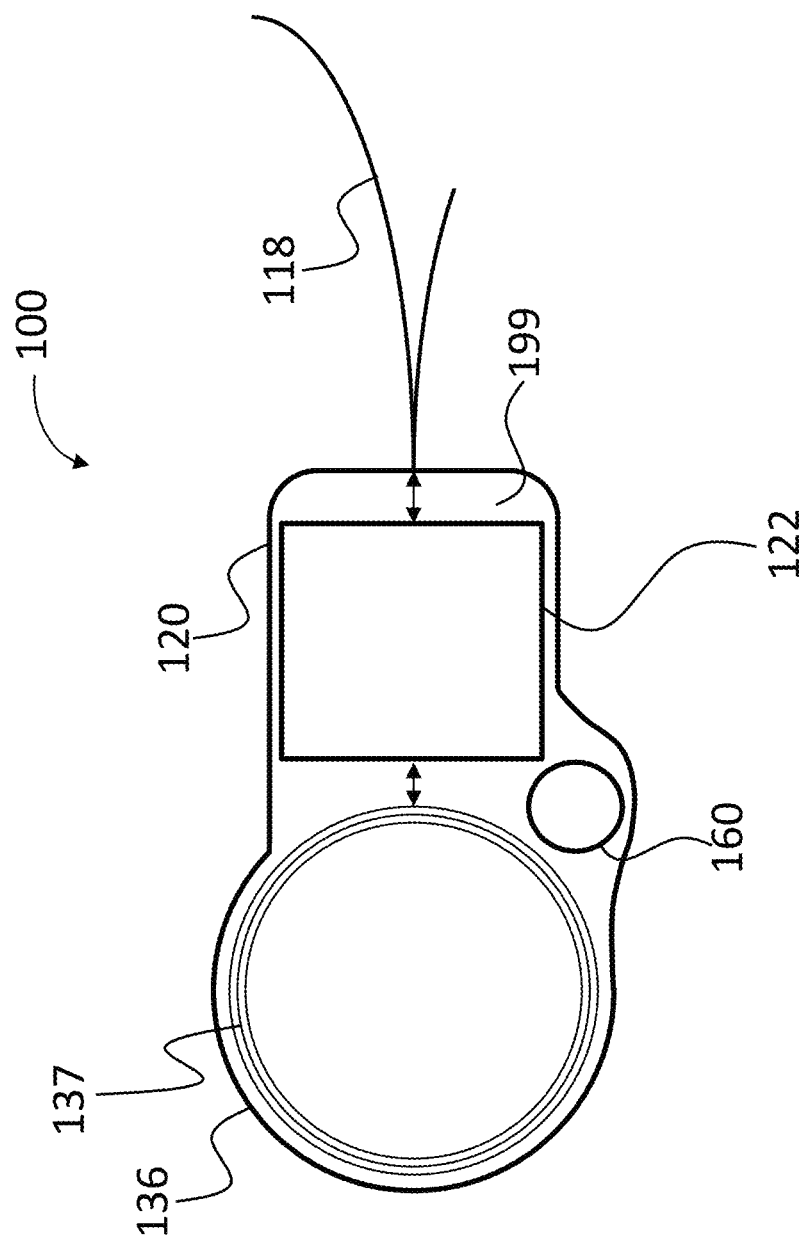

FIG. 7A depicts an exemplary high-level diagram of the implantable component 100 of the system 10, looking downward from outside the skull towards the skull. As can be seen, implantable component 100 includes a magnet apparatus 160, but in contrast to the arrangement of FIG. 1B, the magnet 160 is not surrounded by the coil 137 (the coil is in two-way communication (although in other embodiments, the communication is one-way) with a stimulator unit 122, which in turn is in communication with the electrode assembly 118). As can be seen, the housing 199 extends outward on one side of the implantable component 100 to surround and otherwise envelop the magnet apparatus 160.

Still with reference to FIG. 7A, it is noted that the magnet apparatus 160 is located in a housing made of an elastomeric material 199, such as by way of example only and not by way of limitation, silicone. Hereinafter, the elastomeric material 199 of the housing will be often referred to as silicone. However, it is noted that any reference to silicone herein also corresponds to a reference to any other type of component that will enable the teachings detailed herein and/or variations thereof, such as, by way of example and not by way of limitation only, bio-compatible rubber, etc.

Not depicted in FIG. 7A, the housing made of elastomeric material 199 can include a slit (or slot). In an exemplary embodiment, the slit has utilitarian value in that it can enable insertion and/or removal of the magnet 160 from the housing made of elastomeric material 199. In an exemplary embodiment, tweezers or the like can be inserted into the slit to reach the magnet for withdrawal without removing the other portions of the implantable component 100 from the recipient after implantation. Some additional details of the exemplary slits that can be utilized to enable removal and reimplantation of the magnet 160 will be described in greater detail below. It is further noted that in some alternate embodiments, instead of the slit, an indicia or the like is provided on the housing indicating to the surgeon where the silicone should be cut to reach the magnet so that the magnet can be explanted. That is, instead of the pre-existing slit(s), the surgeon can effectively create the slit in the event that the magnet has to be removed.

FIG. 7B depicts an alternate embodiment, where the magnet apparatus 160 is located in a chassis 164 that is embedded in the silicone housing 199. In this exemplary embodiment, the magnet apparatus 160 is threaded about the outer surface thereof with male threads that interface with female threads of the chassis 164. In an exemplary embodiment, the magnet apparatus 160 is removable from the implantable component 100 by unscrewing the magnet apparatus 160 from the chassis 164. In an exemplary embodiment, torque can be applied via the recessed 162 utilizing a flat head screwdriver or the like. A Phillips wrench can be utilized with embodiments that utilize a hexagon recess. Any arrangement that can enable the magnet apparatus 160 to be removed and/or reattached to the implantable component 100 without removing the implantable component from the recipient can be utilized in at least some exemplary embodiments.

In some exemplary embodiments, the housing completely envelops the chassis 164, and thus the magnet apparatus 160. In some embodiments, the housing envelops only the bottom (the opposite side from that shown in FIG. 7B—the side that faces the skull) and sides, and, in some instances, only a portion of the top of the chassis 164, thus providing an opening for the magnet apparatus to be removed from the housing 199. In some embodiments, the housing 199 completely envelops the chassis 164, and a slit is present, while in other embodiments, a surgeon must create a slit using a scalpel or the like to remove the magnet apparatus 160 from the chassis 164.

It is noted that magnet apparatus 160 is presented in a conceptual manner. In this regard, it is noted that in at least some embodiments, the magnet apparatus 160 is an assembly that includes a magnet surrounded by a biocompatible coating. Still further, in an exemplary embodiment, magnet apparatus 160 is an assembly where the magnet is located within a container having interior dimensions generally corresponding to the exterior dimensions of the magnet. This container can be hermetically sealed, thus isolating the magnet in the container from body fluids of the recipient that penetrate the housing (the same principle of operation occurs with respect to the aforementioned coated magnet). In an exemplary embodiment, this container permits the magnet to revolve or otherwise move relative to the container. Additional details of the container will be described below. In this regard, it is noted that while sometimes the term magnet is used as shorthand for the phrase magnet apparatus, and thus any disclosure herein with respect to a magnet also corresponds to a disclosure of a magnet apparatus according to the aforementioned embodiments and/or variations thereof, and/or any other configuration that can have utilitarian value according to the teachings detailed herein.

Thus, in an exemplary embodiment, there is an implantable medical device, such as the cochlear implant implantable component 100 detailed above, comprising a magnet, such as the magnet of magnet apparatus 160, and an electromagnetic communication wire, such as the inductance coil 137, forming, with respect to two dimensions (e.g., the dimensions of the plane on which FIGS. 7A and 7B are present), an enclosed boundary (i.e., the boundary inside any of the loops of the coil 137). In this exemplary embodiment, the magnet is located outside of the enclosed boundary.

FIG. 8 depicts another exemplary embodiment which includes two magnet apparatuses 160, each of the magnet apparatuses located on an opposite side of the coil 137 in a symmetrical manner, although in other embodiments, the magnets can be located relative to the coil 137 in a non-symmetrical manner. As is the case with the embodiments of FIGS. 7A and 7B, the housing 199 is extended at the locations of the magnet apparatuses 160. In this regard, the features of the housing detailed above with regard to the single magnet apparatus 160 a FIGS. 7A and 7B are also applicable to the embodiment of FIG. 8.

Accordingly, in an exemplary embodiment, there is an implantable medical device, such as that of FIG. 8, wherein there is a first magnet and a second magnet, where the first and second magnets are located outside of the enclosed boundary established by the inductance coil 137.

Figure 9:
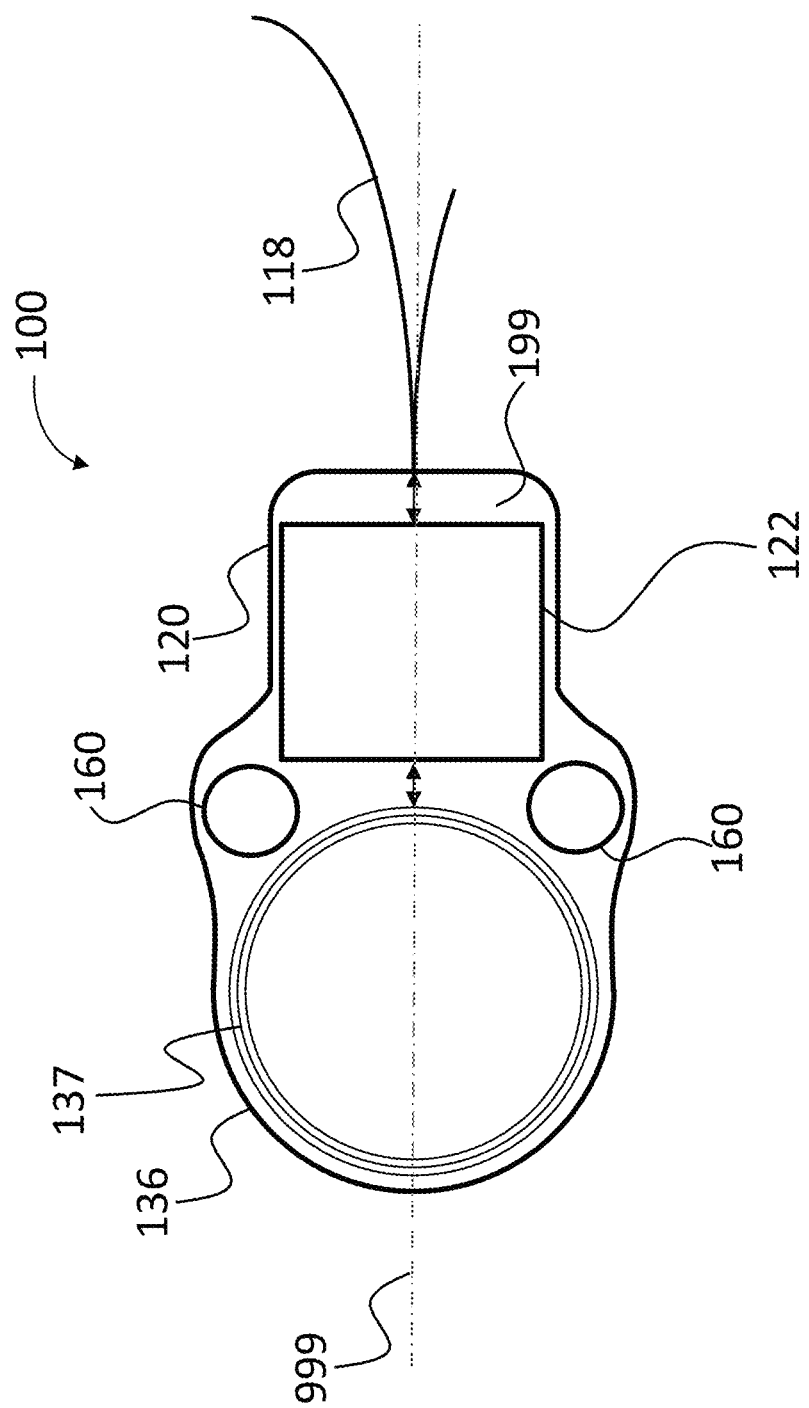

FIG. 9 depicts an alternate embodiment that utilizes a plurality of magnet apparatuses 160, wherein the magnet apparatus 160 is located in a symmetrical manner about the longitudinal axis 999 of the implantable component 100.

Figure 10:
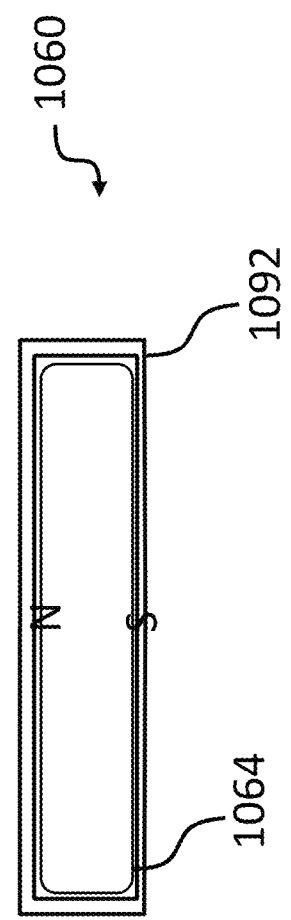
FIG. 10 is an exemplary conceptual schematic of an implantable magnet apparatus according to one embodiment.

FIG. 10 depicts an exemplary magnet apparatus 1060 which is usable as magnet apparatus 160 above.

In an exemplary embodiment, the magnet apparatus 1060 is entirely established by metallic components. That is, there are no non-metallic components that are part of magnet apparatus 1060. Also, the magnet 1064 is not coated, and instead in direct contact with the housing.

Some additional details of magnet apparatus 1060 will now be described.

Herein, any reference to a magnet apparatus refers to a magnet apparatus of any of the embodiments detailed herein unless otherwise indicated. It is briefly noted that back lines have been eliminated in some cases for purposes of ease of illustration. It is further noted that unless otherwise stated, the components of FIG. 10 (and the components of the magnet apparatus detailed herein) are rotationally symmetric about the longitudinal axis, although in other embodiments, such is not necessarily the case.

The magnet apparatus 1060 includes a magnet 1064 which is housed in a titanium housing 1092. Magnet apparatus 1060, when used in the implants detailed herein and other implants (e.g., an implant of an active transcutaneous bone conduction device, an implant of a middle ear actuator, an implant of a heart pace maker, etc.) is removably replaceable to/from the implant, and, in some embodiments, without removing the implant from the recipient, such as for MRI compatibility reasons.

In view of the above, it will be understood that in an exemplary embodiment, there is an implantable medical device, such as a cochlear implant, or any other type of medical device that utilizes an implantable magnet (irrespective of what the implantable magnet is used for/irrespective of whether or not the implantable magnet is utilized to retain an external component to the recipient), comprising a magnet apparatus, such as magnet apparatus 1060 detailed above, including a magnet 1064 encased in a titanium housing 1092. In some instances, the magnet 1064 is coated with a substance, such as, for example, nickel. In any event, in some instances, the magnet apparatus 1060 is entirely established by metallic components.

In an exemplary embodiment, any of magnet apparatuses 160 can correspond to magnet apparatus 1060. Accordingly, in an exemplary embodiment, there is an implantable prosthesis, such as a cochlear implant, comprising an implantable component such as the implantable component 100 of the cochlear implant detailed above, which includes an implantable magnet assembly, such as implantable magnet assembly 1060 detailed above. The magnet assembly 1060 includes a magnet 1064 without plating or a coating, and the magnet assembly includes a housing (e.g., housing 1092) made of titanium, wherein at least a portion of the housing is in direct contact with the magnet 1064 (i.e., the ferromagnetic material that makes up the magnet, as opposed to a coating if such was present).

In an exemplary embodiment, the implantable component is configured to be implanted in a human such that the housing 1092 is exposed to body fluids thereof. That is, with reference to FIG. 1C, as noted above, in an exemplary embodiment, silicone or some other elastomeric material fills or substantially fills the interior of within the dashed line, other than the other components of the implantable device. However, even in embodiments where, for example, slit 180 is not present or is completely sealed (as completely as can be done with respect to silicone), because silicone is permeable to body fluids, body fluids will come into contact with the housing 1092 of the magnet apparatus 1060. That is, in an exemplary embodiment, with respect to typical dimensions of the silicone covering the magnet apparatus 160 of a typical cochlear implant, if the magnet apparatus 1060 was completely encased in silicone, a casing 0.25, 0.5, 0.75, 1, 1.5, 2, 2.5, 3, 3.5, 4, 4.5, 5, 5.5, or 6 mm thick, or even more, with no openings, and implanted in a recipient at the traditional location where a cochlear implant is located (or, more specifically, at the location where the magnet of the implantable component of the cochlear implant is located), body fluids would still come into contact with the housing.

Figure 11:
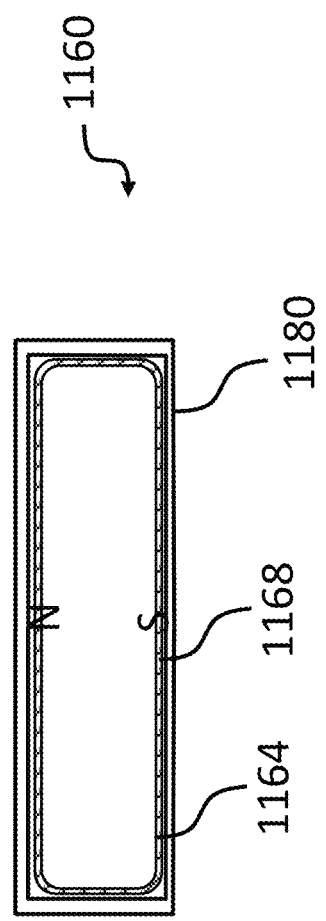
FIG. 11 is an exemplary conceptual schematic of an implantable magnet apparatus according to a completely different embodiment from that of FIG. 10.

FIG. 11 depicts an exemplary magnet apparatus 1160 which is usable as magnet apparatus 160 above.

In an exemplary embodiment, the magnet apparatus 1160 is not entirely established by metallic components. That is, there are non-metallic components that are part of magnet apparatus 1160.

Some additional details of magnet apparatus 1160 will now be described.

The magnet apparatus 1160 includes a magnet 1164 which is housed in a housing 1180, which is a non-titanium housing, and in some embodiments, is a housing made of a polymer. Magnet apparatus 1160, when used in the implants detailed herein and other implants (e.g., an implant of an active transcutaneous bone conduction device, an implant of a middle ear actuator, an implant of a heart pace maker, etc.) is removably replaceable to/from the implant, and, in some embodiments, without removing the implant from the recipient, such as for MRI compatibility reasons. That said, in some other embodiments, it is not removable from the implant.

In view of the above, it will be understood that in an exemplary embodiment, there is an implantable medical device, such as a cochlear implant, or any other type of medical device that utilizes an implantable magnet (irrespective of what the implantable magnet is used for/irrespective of whether or not the implantable magnet is utilized to retain an external component to the recipient), comprising a magnet apparatus, such as magnet apparatus 1160 detailed above, including a magnet 1164 encased in a non-titanium housing 1180. In this embodiment, the magnet 1164 is coated with a substance 1168, such as, for example, nickel.

In an exemplary embodiment, any of magnet apparatuses 160 can correspond to magnet apparatus 1160. Accordingly, in an exemplary embodiment, there is an implantable prosthesis, such as a cochlear implant, comprising an implantable component such as the implantable component 100 of the cochlear implant detailed above, which includes an implantable magnet assembly, such as implantable magnet assembly 1160 detailed above. The magnet assembly 1160 includes a magnet 1164 with a plating/coating 1168, which can be a nickel plating/coating, in some embodiments, and the magnet assembly includes a housing 1180 at least partially devoid of titanium (and in some embodiments, at least partially devoid of metallic substances), and in some embodiments, completely devoid of titanium (and in some embodiments, completely devoid of metallic substances), wherein no portion of the housing is in direct contact with the magnet 1164 (i.e., the ferromagnetic material that makes up the magnet, as opposed to a coating if such was present). In this regard, in this embodiment, the magnet 1160 is plated with a metallic substance (again, nickel in this embodiment).

In an exemplary embodiment, the housing 1180 is made at least in part of a polymer, wherein at least a portion of the housing made out of the polymer is in direct contact with the coating 1168 (e.g., the nickel plating, and thus in direct contact with a metallic substance coating/plating the magnet 1164). In an exemplary embodiment, the implantable component is configured to be implanted in a human such that the housing 1180 is exposed to body fluids thereof.

As with the embodiment of FIG. 10, in an exemplary embodiment of the embodiment of FIG. 11, the implantable component is configured to be implanted in a human such that the housing 1080 is exposed to body fluids thereof. That is, with reference to FIG. 1C, as noted above, in an exemplary embodiment, silicone or some other elastomeric material fills or substantially fills the interior of within the dashed line, other than the other components of the implantable device. However, even in embodiments where, for example, slit 180 is not present or is completely sealed (as completely as can be done with respect to silicone), because silicone is permeable to body fluids, body fluids will come into contact with the housing 1180 of the magnet apparatus 1160. That is, in an exemplary embodiment, with respect to typical dimensions of the silicone covering the magnet apparatus 160 of a typical cochlear implant, if the magnet apparatus 1160 was completely encased in silicone, a casing 0.25, 0.5, 0.75, 1, 1.5, 2, 2.5, 3, 3.5, 4, 4.5, 5, 5.5, or 6 mm thick, or even more, with no openings, and implanted in a recipient at the traditional location where a cochlear implant is located (or, more specifically, at the location where the magnet of the implantable component of the cochlear implant is located), body fluids would still come into contact with the housing.

In an exemplary embodiment of the implantable prosthesis using magnet apparatus 1160, the magnet 1164 is covered by plating and/or metallization (as opposed to a separate plate/housing), established by the metallic substance. In some embodiments, the plating/metallization has imperfections or faults, such as by way of example only and not by way of limitation, pin holes, therein. In this exemplary embodiment, the imperfections are such that the magnet 1164 in general, and the ferromagnetic material thereof in particular, would be exposed to body fluids when implanted in a recipient, even if encased in the aforementioned exemplary silicone encasement. (In an exemplary embodiment, the magnet 1164 is made of a rare earth such as, for example, NbFeB or SmCo.)

However, owing to the utilization of housing 1180, in some exemplary embodiments, a barrier, albeit not perfect, as will be detailed below, prevents substantial amounts of body fluids (including, in some embodiments, all amounts of body fluids) from reaching magnet 1164 via the imperfections/prevents corrosion effective amounts of body fluids from reaching magnet 1164 via the imperfections (effective enough to cause corrosion of the magnet 1164 requiring explantation). In an exemplary embodiment the magnet is made of a material that readily corrodes when exposed to body fluids.

In an exemplary embodiment, the magnet is configured to be protected from the body fluids by a barrier consisting of the polymer of the housing 1180 and the metallic substance 1168 or the magnet 1164 is configured to be protected from the body fluids by a barrier consisting essentially of the polymer of the housing 1180 and the metallic substance 1164.

Figure 12:
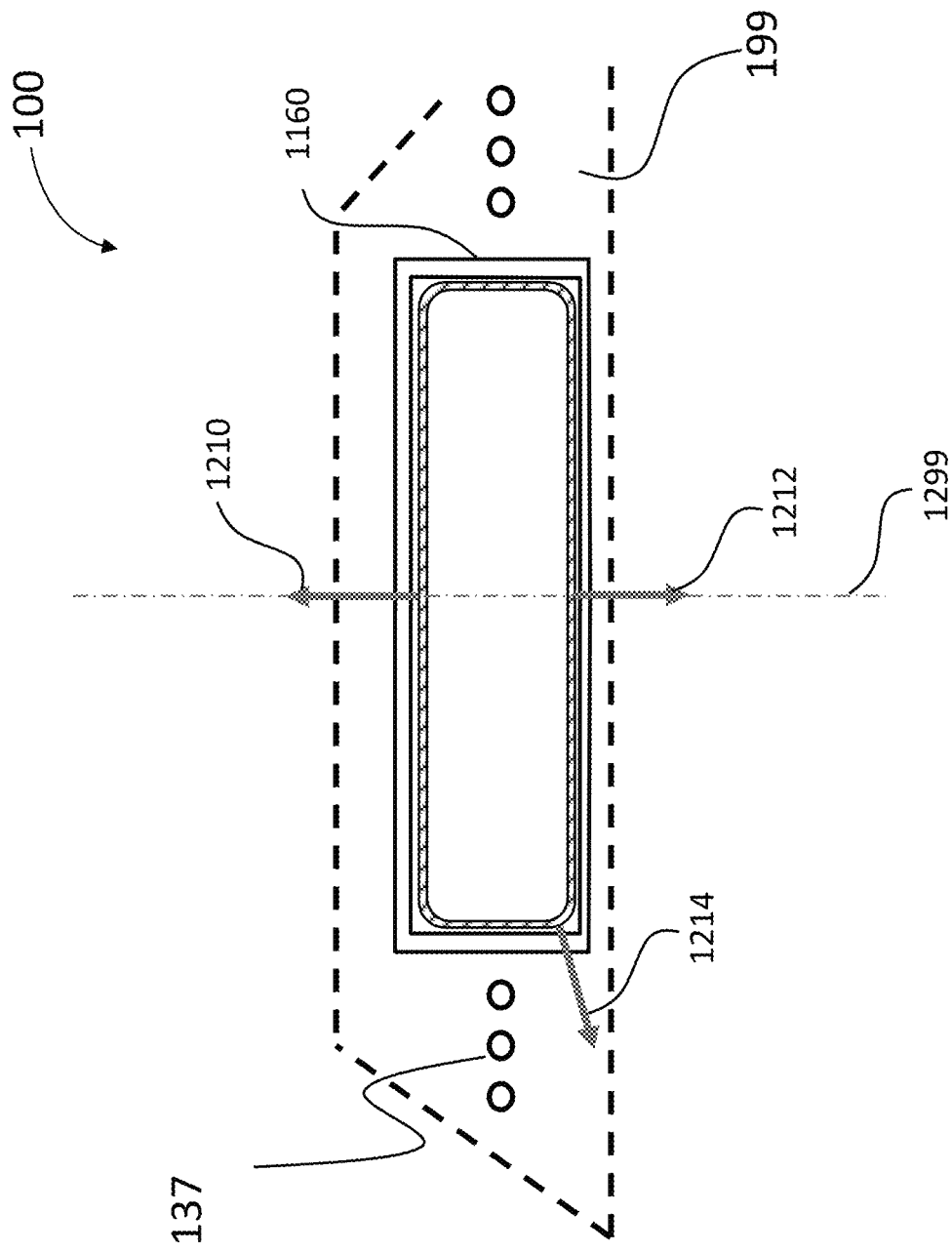
FIGS. 12 and 13 present some exemplary details of utilization of the embodiment of FIG. 11.

In an exemplary embodiment, the implantable magnet assembly 1160 is devoid of metals and devoid of ceramic materials covering the plating/metallization established by the metallic substance. For example, the housing 1180 is devoid of metal and devoid of ceramic materials. In an exemplary embodiment, after implantation, with respect to a plane parallel to and lying on the longitudinal axis of the magnet assembly 1160 (e.g., the plane of the page of FIG. 11 and FIG. 12), there is no metal and no ceramic along a vector starting from the surface of the plating to the exterior surface of the implantable component (e.g., the surface of the silicone body of the implantable component 100). This is represented by FIG. 12 by way of concept, which depicts a portion of the implantable component 100, where longitudinal axis 1299 is the longitudinal axis of the magnet apparatus 1160, and vector 1210 extends from the surface of the plating 1168 through housing 1180 and through the silicone elastomer 199 into the surrounding body tissue of the recipient. Vectors 1212 and 1214 extend in a similar manner. Each of these vectors extend from the surface of the nickel plating 1168 through the remaining components of the implant 100 to body tissue without extending through a metallic component/metal component and/or without extending through ceramic materials. That said, with respect to a vector that might be normal to vector 1210, it can be seen that a scenario exists where the vector will extend through the coil 137, which coil is metal, and thus this criteria would not apply. However, this criteria does not include all vectors, but only some vectors. That said, in an exemplary embodiment, the vector is a vector that extends from the surface of the plating to the beginning of the elastomeric material 199, and thus with respect to the plane of FIG. 12 (i.e., the plane of the paper upon which FIG. 12 is printed), such would encompass all vectors, because elastomeric material is interposed between the magnet apparatus 1160 and the coil 137.

Figure 13:
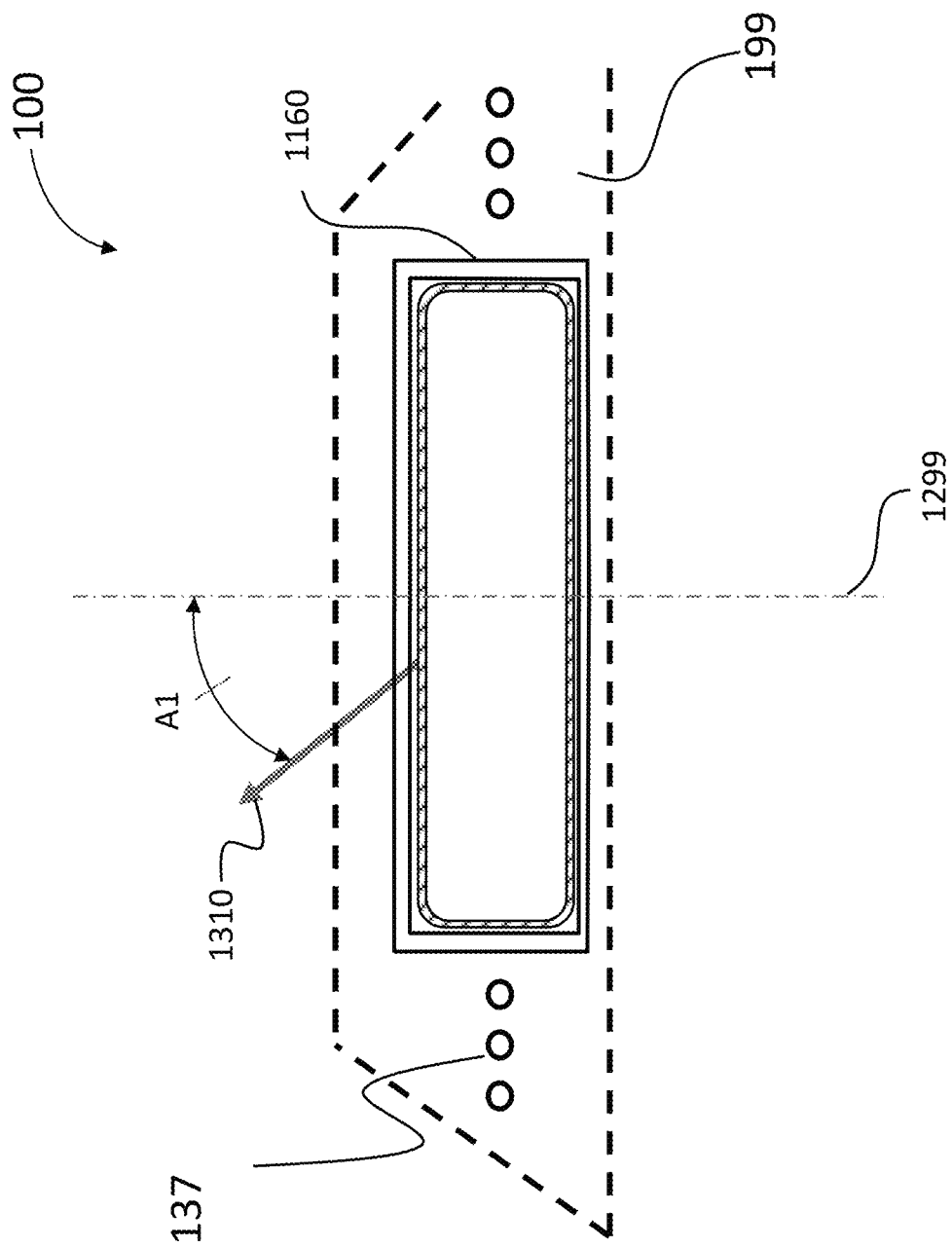

FIG. 13 presents a conceptual diagram that presents a vector 1310 extending from a surface of the plating of the magnet apparatus 1160, which vector, if extrapolated into the interior of the magnet apparatus, would extend through the geometric center thereof. Vector 1310 is at an angle A1 from the longitudinal axis 1299 of the magnet apparatus, which extends to the geometric center. With respect to the plane of FIG. 13 (i.e., the paper upon which FIG. 13 is printed), the plane lying on and parallel to the longitudinal axis 1299, there is a vector that is at an angle A1 lying on that plane that meets the above-noted criteria (the vector extends from the surface of the plating to the tissue of the recipient without extending through metal and/or ceramic material). In an exemplary embodiment, there is an implantable component that has such vectors for values of A1 for each of 45, 40, 35, 30, 25, 20, 15, 14, 13, 12, 11, 10, 9, 8, 7, 6, 5, 4, 3, 2, or 1 degree increments (e.g., ever 10 degrees from the longitudinal axis, there is a vector that meets this criteria). In an exemplary embodiment, there is an implantable component where, with respect to angles on the plane of FIG. 13, the cumulative angles based on A1 can equal 359, 358, 357, 356, 355, 354, 353, 352, 351, 350, 349, 348, 347, 346, 345, 344, 343, 342, 341, 340, 339, 338, 337, 336, 335, 334, 333, 332, 331, 330, 329, 328, 327, 326, 325, 324, 323, 322, 321, 320, 315, 310, 305, 300, 295, 290, 285, 280, 275, 270, 260, 250, 240, 230, 220, 210, 200, 190, 180, or 170 degrees in totality while meeting the above criteria (e.g., other than an arc of 5 degrees on either side (the arc that encompasses the coils 137), the above criteria is met, and thus the cumulative angle is 350 degrees meeting the above criteria (the vector extends from the surface of the plating to the tissue of the recipient without extending through metal and/or ceramic material). Note that the above can also be the case for a plane that is normal to the longitudinal axis 1299 and passes through the geometric center of the magnet apparatus 1160.

In an exemplary embodiment, there is an implantable component that vectors over all values of A1 with respect to not passing through metal and/or not passing through ceramic material with respect to a vector extending from the surface of the plating of the magnet apparatus 1160 to the beginning of the elastomeric material 199. In an exemplary embodiment, there is an implantable component where, with respect to angles on the plane of FIG. 13, the cumulative angles based on A1 can equal 360, 359, 358, 357, 356, 355, 354, 353, 352, 351, 350, 349, 348, 347, 346, 345, 344, 343, 342, 341, 340, 339, 338, 337, 336, 335, 334, 333, 332, 331, 330, 329, 328, 327, 326, 325, 324, 323, 322, 321, 320, 315, 310, 305, 300, 295, 290, 285, 280, 275, 270, 260, 250, 240, 230, 220, 210, 200, 190, 180 or 170 degrees in totality with respect to not passing through metal and/or not passing through ceramic material with respect to a vector extending from the surface of the plating of the magnet apparatus 1160 to the beginning of the elastomeric material 199. Note that the above can also be the case for a plane that is normal to the longitudinal axis 1299 and passes through the geometric center of the magnet apparatus 1160.

As noted above, in some embodiments, the implantable magnet assembly 1160 is configured to be removably inserted into an implantable portion of a hearing prosthesis (e.g., implantable component 100, via slit 180).

In view of the above, it can be seen that in an exemplary embodiment, there is an implantable prosthesis, comprising an implantable functional component including an implantable first housing and an implantable magnet assembly, the first housing having electronics located therein. In an exemplary embodiment, this implantable functional component can be an implantable functional component of a pacemaker, an implantable functional component of a retinal prosthesis, an implantable functional component of a prosthetic limb, etc. however, for the following, this will be detailed in terms of an implantable functional component of a hearing prostheses, such as an implantable functional component of a middle ear implant, an implantable component of an active transcutaneous bone conduction device and an implantable component of a cochlear implant. Indeed, the latter will be the focus of the following disclosure.

In an exemplary embodiment, the first housing can be the housing 122 of the implantable component 100 as detailed above in FIGS. 1B and 1C. In an exemplary embodiment, the implantable magnet assembly can be the magnet apparatus 160 (and thus any of the magnet apparatuses detailed herein—reference to magnet apparatus 160 corresponds to reference to any of the other magnet apparatuses herein and vice versa). In an exemplary embodiment, the electronics located in housing 122 corresponds to that of a stimulator unit of a cochlear implant. In an exemplary embodiment, the electronics located in housing 122 can correspond to a processor as well, such as in an embodiment where the cochlear implant is a totally implantable hearing prosthesis. In an exemplary embodiment, housing 122 includes electronics for a middle ear implant (e.g., the electronics that are utilized to output a control signal of an actuator for a middle ear implant). Housing 122 can include electronics for an active transcutaneous bone conduction device (e.g., the electronics that are utilized to output a control signal of an actuator for the active transcutaneous bone conduction device). The electronics can be diodes, resistors, capacitors, integrated circuits, control chips, etc.

In an exemplary embodiment, the magnet assembly includes a plated magnet located in a $2^{nd}$ housing (e.g., the magnet assembly can correspond to the magnet apparatus 1160 of FIG. 11). In this exemplary embodiment, the second housing (e.g., housing 1180) is established by structural components that are non-metallic and man-made synthetic components. In an exemplary embodiment, the $2^{nd}$ housing (e.g., housing 1180) is established by structural components that are based on carbon and/or silicone chains. By "established," it is meant that that is the main component (e.g., a scenario where the housing is established by polymer, but there are titanium reinforced structural components embedded in the polymer—analogy, reinforced concrete is established by concrete, even though there is located rebar therein).

In an exemplary embodiment, the magnet assembly includes only one housing, wherein the only one housing corresponds to the $2^{nd}$ housing. With respect to the embodiment of FIG. 11, it is to be understood that the plating 1168 is not a housing. In an exemplary embodiment, the $2^{nd}$ housing consists essentially of a polymer, such as PEEK, etc.

It is noted that in some embodiments, the implantable prosthesis is configured to enable the magnet assembly to be removed, as a complete assembly, from the implantable functional component while the implantable functional component is implanted in the recipient. For example, the slit 180 can be used to access the magnet assembly. As will be detailed below, in an exemplary embodiment, the housing 1160 has formed therewith a component that facilitates removal.

Figure 14:
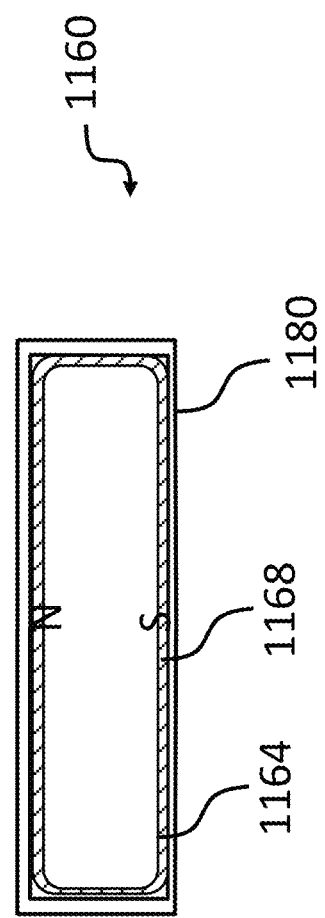
FIG. 14 presents another exemplary embodiment of an implantable magnet apparatus.

With reference to FIG. 11, it can be seen that there is a space between the plating 1168 and the inside of the housing 1180. Conversely, in FIG. 14, the plating 1168 is in direct contact with the inside of the housing 1180 with respect to the top and bottom walls. This, in an exemplary embodiment, the second housing is in direct contact with the plating of the magnet. Still further, in some exemplary embodiments, the housing 1180 is in direct contact with the plating at all locations over the surface thereof. In an exemplary embodiment, X of the surface area of the plating is in direct contact with the housing 1180, where X is 20%, 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% or any value or range of values therebetween in 0.1% increments (e.g., 72.3% to 92.4%, 44.4%, etc.). In an exemplary embodiment, X of the surface area of the interior of the housing is in direct contact with the plating.

In some embodiments, the magnet assembly is supported in the implantable prosthesis directly via a silicone body in direct contact with the second housing (and, in some embodiments, in direct contact with the first housing, such as for embodiments such as the embodiment of FIG. 1C where the silicone body is one single component—however, in some other embodiments, such as where the housing containing the electronics as separate and offset from the coil (e.g., where the coil is a separate unit and is in signal communication with the first housing via electrical lead that extends from that unit to a unit of which the first housing is a part), and thus the silicone body is only in direct contact with the $2^{nd}$ housing and not in direct contact with the first housing). In an exemplary embodiment, the magnet assembly 1162 is devoid of metallic components other than the magnet and the plating thereof and is devoid of ceramic materials.

In some embodiments, the magnet assembly is supported in the implantable prosthesis indirectly via a silicone body that surrounds or substantially surrounds (which includes completely surrounds) the magnet assembly (and, in some embodiments, surrounds or substantially surrounds the first housing, such as for embodiments such as the embodiment of FIG. 1C where the silicone body is one single component—however, in some other embodiments, such as where the housing containing the electronics as separate and offset from the coil (e.g., where the coil is a separate unit and is in signal communication with the first housing via electrical lead that extends from that unit to a unit of which the first housing is a part), and thus the silicone body only surrounds or substantially surrounds the $2^{nd}$ housing and does not substantially surround the first housing). In an exemplary embodiment, the magnet assembly 1162 is devoid of metallic components other than the magnet and the plating thereof and is devoid of ceramic materials. An exemplary embodiment of this will now be detailed.

Figure 15:
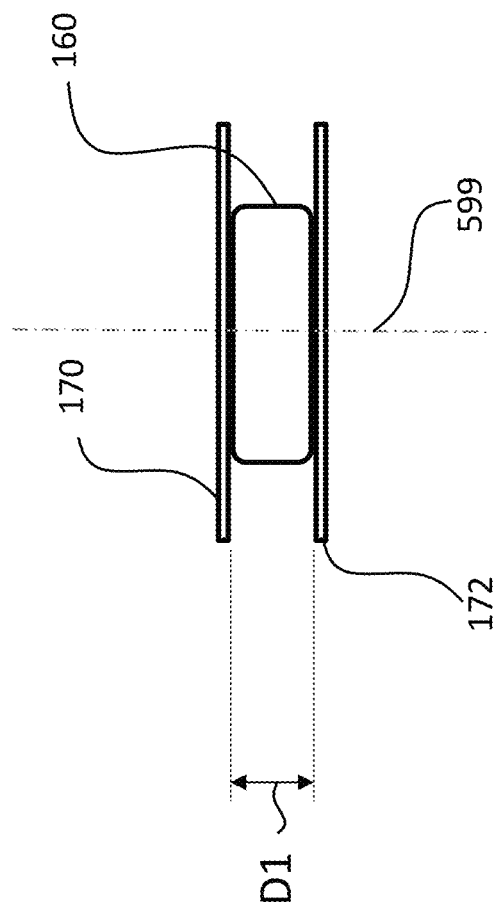
FIGS. 15 to 18 present various exemplary embodiments of utilization of an exemplary magnet apparatus.
Figure 16:
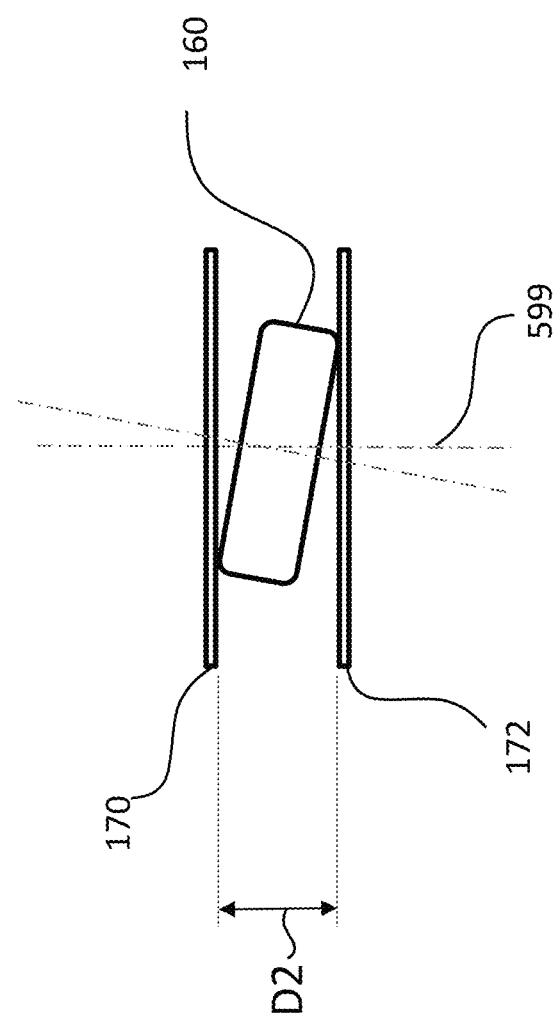

With respect to indirect support, it is noted that in some exemplary embodiments, the device is configured to enable the magnet apparatus 160 to tilt relative to the wire of coil 137 and/or change a distance relative to the wire of the coil 137. That is, the magnet can move out of the plane of the magnet. With regard to tilting, in an exemplary embodiment, plates sandwich a disk magnet, and the plates permit the disk of the magnet to tilt. In this regard, in an exemplary embodiment, the arrangements of U.S. Patent Application No. 62/174,788, filed on Jun. 12, 2016, to Roger Leigh as an inventor, entitled Magnet Management MRI Compatibility, can be utilized with the magnet apparatuses herein. Briefly, FIG. 15 depicts an exemplary embodiment utilizing plates 170, where an elastomeric material such as the silicon of the housing surrounds the plates and holds the plates in place against the magnet 160. As can be seen, the plates 170 and 172 are located a distance D1 from each other. In an exemplary embodiment, distance D1 corresponds to the thickness of the magnet (as differentiated from the width of the magnet, which corresponds to the diameter of a disc magnet, which can be a disk magnet, as measured on a plane normal to the longitudinal axis 599). That is, in an exemplary embodiment, the plates are located in direct contact with the opposite faces of the magnet apparatus 160. In an exemplary embodiment where the opposite faces of the magnet apparatus are parallel, the surfaces of the plates 170 and 172 facing each other are also parallel, as those surfaces are also flat surfaces. As noted above, the elastomeric material surrounding the plates holds the plates against the magnet apparatus 160. That is, in an exemplary embodiment, the housing made from elastomeric material 199 is arranged such that when the magnet apparatus 160 is located between the plates, the elastomeric material can impart a downwards and upwards force, respectively, onto the plate 170 and plate 172, thereby imparting a downward and upward force on to the opposite faces of the magnet apparatus 160. When the magnet(s) are exposed to a magnetic field, such as in an MRI machine, in an exemplary embodiment, as seen in FIG. 16, the implantable component 100 is configured such that the plates 170 and 172 are pushed apart from one another due to rotation of the magnet apparatus 160 as a result of the torque applied thereto due to, for example, a 3 T magnetic field. As can be seen, the magnet apparatus 160 rotates such that its longitudinal axis moves from its normal position (the position where the magnet is located in the absence of an external magnetic field. The plates separate a distance D2, which is greater than D1.

Alternatively, and/or in addition to this, the magnet apparatus 160 can move horizontally (left and right relative to the frame of reference of FIGS. 12 and 13). Thus, in an exemplary embodiment, the implantable component 100 is configured to enable the magnet to change a distance relative to the wire of the coil 137.

In any event, because the plates 170 and 172 are interposed between the elastomeric body 199 and the magnet apparatus 160, in this exemplary embodiment, the magnet apparatus 160 is only indirectly supported by the elastomeric body 199.

Figure 17:
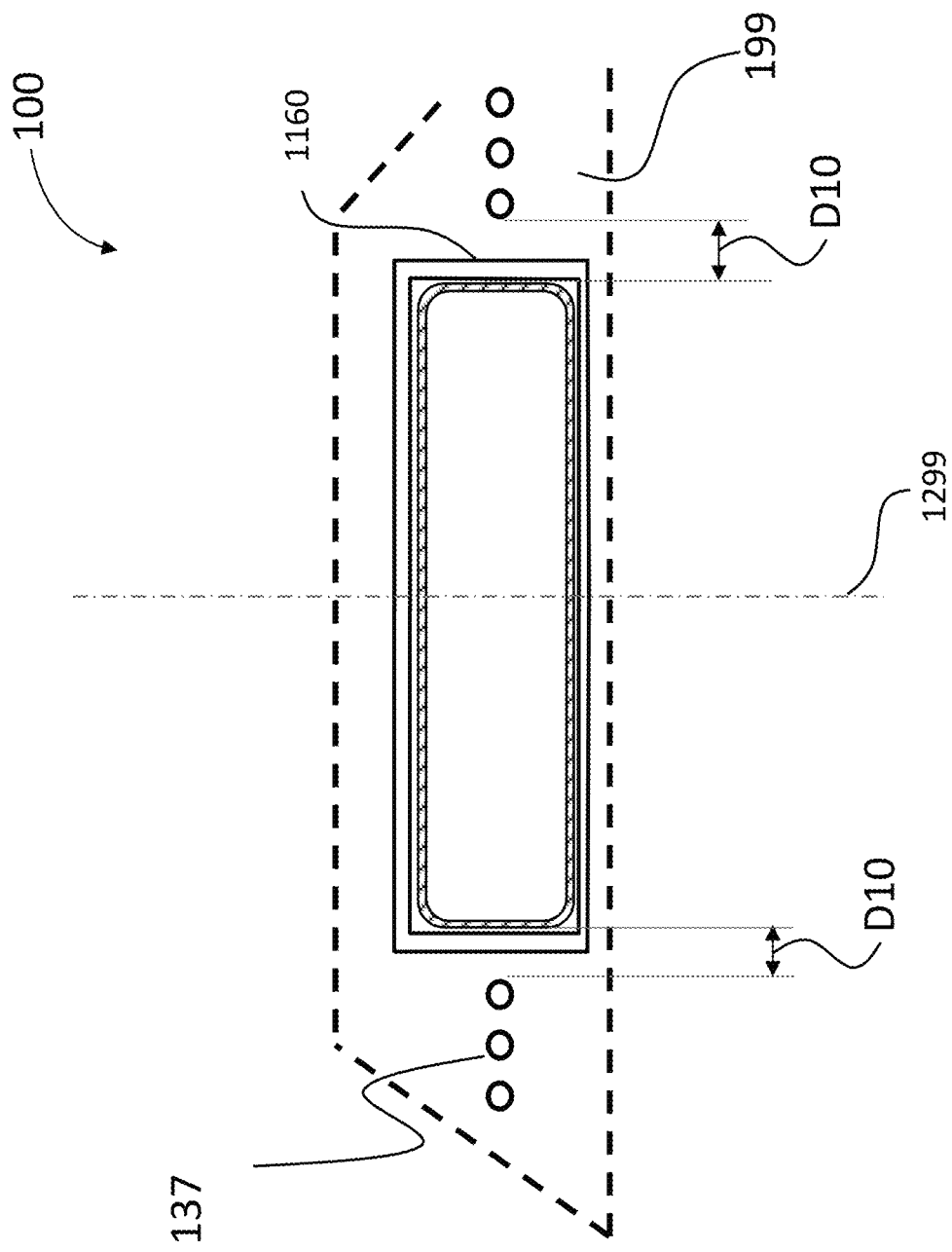

In some embodiments, the magnet assembly 1160 is supported in the implantable prosthesis via a substantially silicone body (e.g., directly or indirectly), which body also supports an RF inductance coil (e.g., coil 137), which, in some embodiments, is directly embedded in the silicone of the body, and thus in direct contact with the coil (where the coil can be a pure metallic component or a metallic component coated with a non-metallic but electromagnetically permeable material). In an exemplary embodiment, with respect to components of the implantable prosthesis located inboard of the RF inductance coil and outboard of the plated magnet (e.g., the space spanning the distances D10 in FIG. 17, and if viewed from the reference of FIG. 1B, the area between the plated magnet and the innermost turn of the coil 137), the components have a hardness on the Shore A scale of less than Y, where Y can be any value less than 120 A, 110 A, 100 A, 95 A, 90 A, 89, 88, 87, 86, 85, 84, 83, 82, 81, 80, 70, 78, 77, 76, 75, 74, 73, 72, 71, 70, 69, 68, 67, 66, 65, 64, 63, 62, 61, 60, 59, 58, 57, 56, 55, 54, 53, 52, 51 or 50 A or less.

Figure 18:
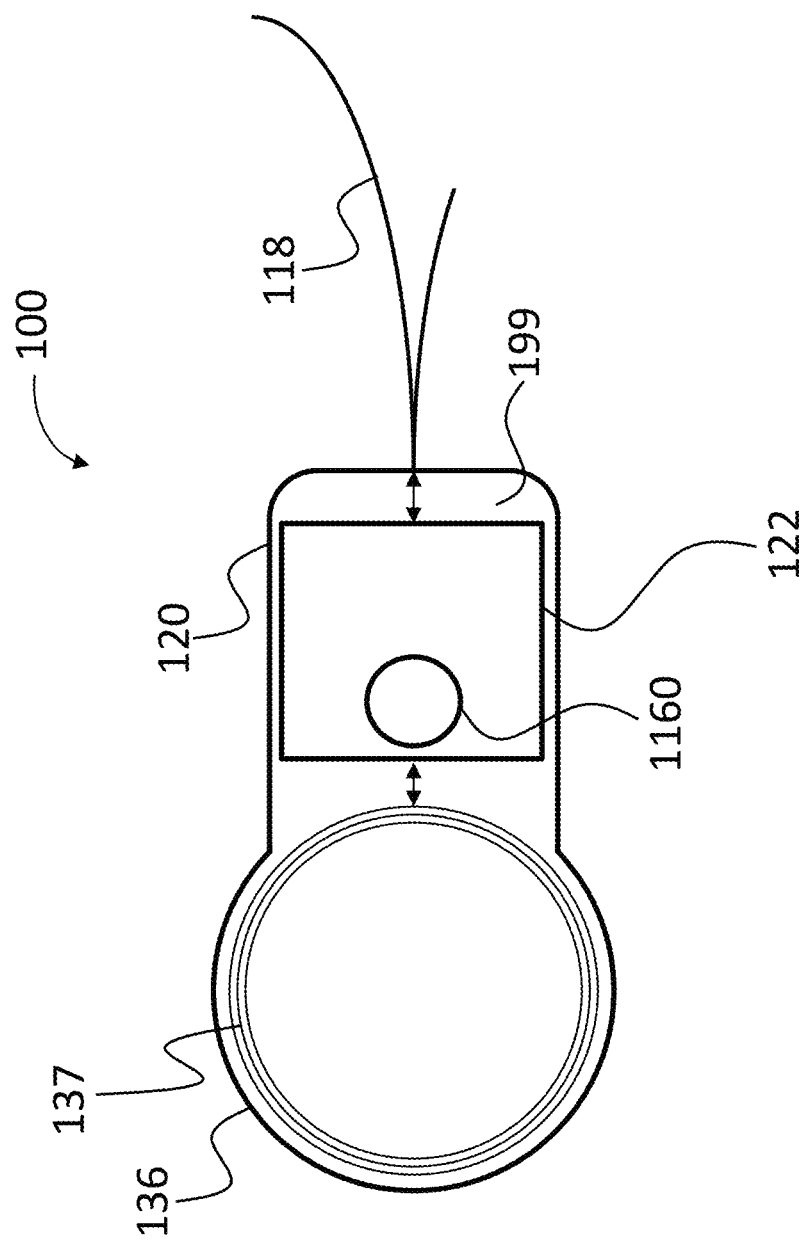

FIG. 18 depicts an alternate embodiment of an implantable component 100, where the magnet apparatus 1160 is located outside of the enclosed area of the coil 137, but also located within the general boundaries of the housing 122 (which housing can include the electronics for the functional component as noted above). In an exemplary embodiment, the housing 122 is a titanium housing that completely envelops the magnet 160 (making the magnet unremovable in at least some exemplary embodiments). That is, in an exemplary embodiment, the magnet is fully inside the housing 122. In an exemplary embodiment, the magnet is fully hermetically sealed inside the housing 122. That said, in an alternate embodiment, the housing contains a recess into which at least a portion of the magnet apparatus 1160 is located. By way of example only and not by way of limitation, the housing can include a through hole (or through tunnel), where the walls of the hole (tunnel) form walls of the housing that permit the inside of the housing to remain hermetically sealed despite a hole passing through the housing from one side to the other. That said, in an exemplary embodiment, the hole only goes through a portion of the thickness of the housing. In an exemplary embodiment, the hole can be female threaded to receive threads of the magnet apparatus 1160 so that the magnet apparatus 1160 can be screwed in and out of the housing, thus enabling removal and re-insertion of the magnet apparatus 160 to and from the housing 122, and thus to and from the implantable component 100. In an exemplary embodiment, the housing 199 completely envelops the housing 122 and the magnet 1160. In an exemplary embodiment, the housing 199 stops at the edges of the hole for the magnet apparatus 1160. In an exemplary embodiment, the housing 199 extends over a portion of the magnet beyond the boundary of the magnet. In an exemplary embodiment, there is a slit in the housing 199 to enable the magnet to pass through the housing 199. Any arrangement that can enable the magnet apparatus to be removed and replaced can be utilized in at least some embodiments. It is noted that the aforementioned configurations can be utilized even if the magnet apparatus is not intended to be removable/replaceable.

As noted above, the implantable component is used with an external component, either where the external component is a sound processor apparatus and/or a sound capture device, or where, in the case of a totally implantable hearing prosthesis, where the external component is a charging system, etc. Accordingly, in an exemplary embodiment, there is a prosthesis system, such as system 10, which includes an implantable prosthesis according to any one or more of the embodiments detailed herein, such as implantable component 100, and an external component, such as external component 142 detailed above, the external component including a first RF inductance coil 130 and a second magnet assembly (not shown in FIG. 1A) including a second magnet concentrically located within the first RF inductance coil 130. The magnet arrangement between the first and second magnet assemblies can be that of FIG. 5 or FIG. 6, where the first magnet assembly is magnet assembly 160 and the second magnet assembly is magnet 560. In this particular exemplary embodiment, the plated magnet of the first magnet assembly 160 is concentric with a second RF inductance coil of the implantable functional component (e.g., concentric relative to axis 599). Also, the prosthesis system 10 is configured to establish inductance communication between the first RF inductance coil and the second RF inductance coil, concomitant with the teachings detailed above. Moreover, the prosthesis system 10 is configured to establish a magnetic coupling between the second magnet and the plated magnet so as to place the second RF inductance coil 130 of the external component 142 in a substantially concentric orientation with the first RF inductance coil 137 of the implantable functional component 100 via a magnetic field path extending from the surface of the plated magnet of the implantable functional component 100 to the surface of the second magnet assembly 560 that passes only through water based substances (e.g., body fluids, etc.), carbon based substances (e.g., skin, the housing 1180, the plate 170, etc.) and/or silicon based substances (e.g., silicone of body 199). Also, it is noted that in an exemplary embodiment, the second magnet of the second magnet assembly is also plated, and the magnetic field path extending from the plated magnet to the second magnet assembly extends from the plating of the plated magnet assembly to the plating of the second magnet without passing through a metallic component.

In an exemplary embodiment, there is an implantable magnet assembly, such as assembly 1160, which includes a magnet (e.g., magnet 1164) coated with a substance (e.g., the plating 1168), the magnet being located in a housing (e.g., housing 1180). In this embodiment, the implantable magnet assembly is configured to be implanted in a human such that the housing is exposed to body fluids thereof (e.g., because the silicone of the body 199 is permeable to such fluids, etc.), and the assembly is configured to protect the magnet from body fluids via a system that consists of the substance that coats the magnet and one or more non-metallic pliable components (or flexible components or non-brittle components or compliant components, etc.). In some embodiments of this embodiment, as noted above, the implantable magnet assembly consists of the magnet and the housing and/or, in some embodiments, the housing is made of a non-metallic, non-ceramic, substance (e.g., a polymer, such as PEEK, etc.). In an exemplary embodiment, the substance coating the magnet is plating, which can be, for example, a Ni—Cu—Ni multilayer combination, Ni—Cu—Au—with the top layer being gold, which can work well in water applications. Thus, in some embodiments, the plating is a nickel-based plating. Any substance coating the magnet that can enable the teachings detailed herein can be used.

The implantable assembly, in some embodiments, is configured to protect the magnet from body fluids via a system that consists of the substance that coats the magnet and the housing. Consistent with the teachings above, the housing can be a non-metallic housing and/or a non-ceramic housing. The housing can be made of a non-metallic, non-ceramic, substance. By "made of," it is meant that at least about 80% by volume of the housing is a non-metallic, non-ceramic, substance. (Some embodiments are such that at least Z by volume of the housing is a non-metallic, non-ceramic substance, where Z is 51%, 55%, 60%, 65%, 70%, 75%, 80%, 81, 82, 83, 84, 85, 86, 87, 88, 89, 90, 91, 92, 93, 94, 95, 96, 97, 98, 99, or 100%.)

In some exemplary embodiments, other than the magnet and the substance that coats the magnet, the implantable magnet assembly is devoid of metallic components, although in some embodiments, the housing proper is devoid of metallic components—component attached to the housing, such as a handle, can be metallic (by way of example only and not by way of limitation, in an exemplary embodiment, the housing proper can be a polymer that is molded about the coated magnet, where during the molding process, a metallic handle is attached to the polymer housing. In some embodiments, the handle can be fixedly located relative to the coated magnet in the mold when the polymer is molded thereabout, such as by way of example only and not by way of limitation, via an injection molding process, etc.). In some embodiments, the implantable magnet assembly is devoid of ceramic components, although in some embodiments, the housing proper is devoid of ceramic components—a component attached to the housing, such as a handle, can be ceramic, positioned and located in the manner just described, for example, for the metallic handle. It is also noted that in some embodiments, the panels can be included in the magnet apparatus after the housing is molded (e.g., by welding, by adhesive, by screwing therein, etc.)

Figure 19:
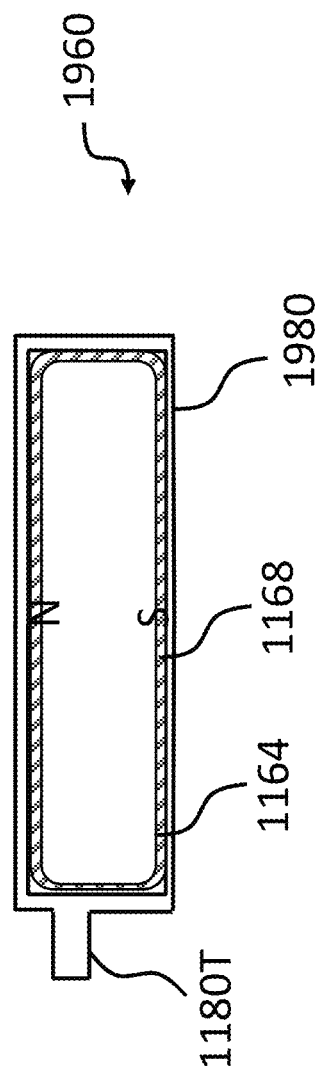
FIG. 19 presents an exemplary embodiment of an exemplary magnet apparatus.

That said, with respect to the handles, in some embodiments, the handle is a handle that is a monolithic component with the housing proper. For example, in an exemplary embodiment, the housing is a polymer molded component that includes a grip tongue that is monolithic with a portion of the housing (the housing proper) that encapsulates the magnet. An embodiment of this is seen in FIG. 19, where implantable magnet apparatus 1960 includes housing 1980. Implantable magnet apparatus 1960 also includes the tongue 1980T that is monolithic with the rest of the housing 1980 (the housing proper). In an exemplary embodiment, the tongue in 1980T has utilitarian value with respect to enabling a surgeon or other healthcare professional to reach through the slit 180 with a surgical tweezers or the like and grip the tongue 1980T to withdraw all the magnet apparatus 1960 from the implantable component (and to grip the tongue 1980T with a tweezers for insertion through the slit 180 to insert the apparatus 1960 into the implantable component 100). In an exemplary embodiment, tongue 1980T extends through a slot 180, and tongue 1980T fills the opening of the slot. In an exemplary embodiment, other components can be integrated into the housing, alternatively or including the tongue/handle, etc. For example, components that help secure the magnet apparatus in the silicone can be used (bumps, hooked-shaped components, etc.).

An exemplary embodiment includes a method associated with a magnet apparatus. The method can include obtaining access to a recipient having a magnet implanted in him or her. The method can also include establishing or breaking a magnetic attractive field between a first magnet of an external component of a prosthesis (e.g., the magnet 560) and a second magnet of an implanted component of the prosthesis (e.g., magnet 1064). In an exemplary embodiment, this can include removing the external component 142 from the head of the recipient, or placing the external component 142 against the head of the recipient. In this exemplary method, a portion of a magnetic path of the magnetic attractive field that extends between the first magnet and the second magnet extends through the recipient to the second magnet passing though at most only carbon based substances, silicon based substances, water based substances, air, and a metallic coating of the second magnet. In this regard, this portion of the path is the portion that extends through the recipient, and is between the first magnet and the second magnet, as just noted. This does not mean that the portion of the path must extend all the way from the first magnet to the second magnet, only that the portion of the path extend through the recipient and between the first and second magnets. This as opposed to a path or a portion of a path that extends from the first magnet the second magnet, as will be described below.

Figure 20:
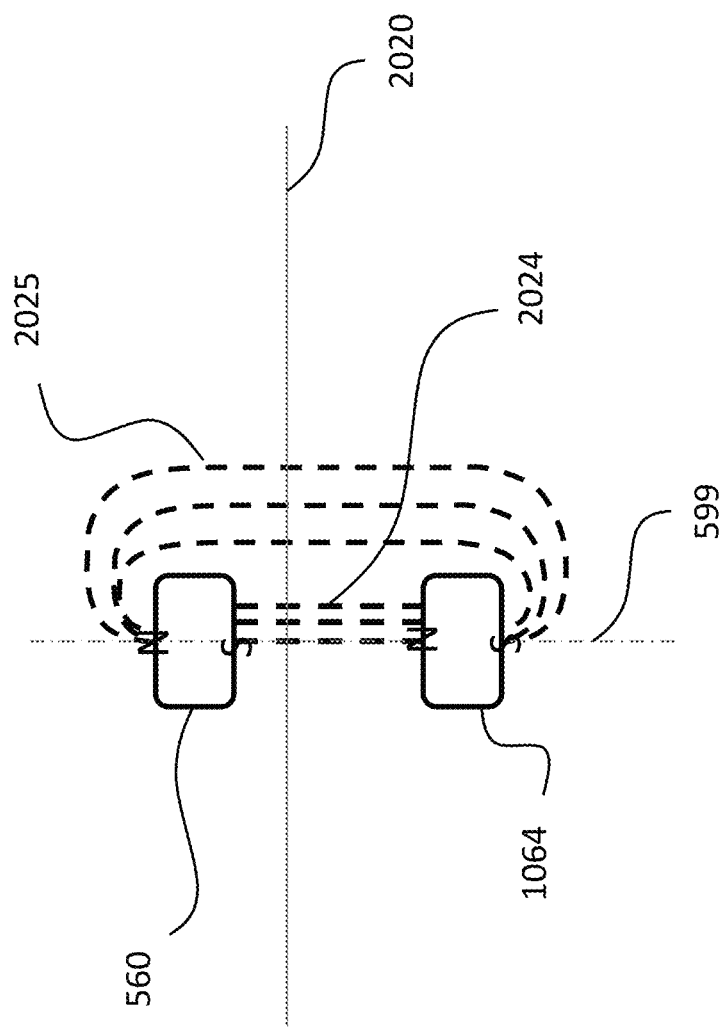
FIG. 20 presents an exemplary magnetic attraction field according to an exemplary embodiment presented in a conceptual manner.

Also, it is noted that the aforementioned described path is but one of many paths that exist with respect to the magnetic attractive field between the first and second magnets. By way of example only and not by way of limitation, referring now to FIG. 20, which depicts an exemplary embodiment of a magnetic attractive field, or more accurately, a portion thereof (the field would be symmetrical about the longitudinal axis 599, in at least some exemplary embodiments), it can be seen that there is a path 2024 that extends between magnet 560 and magnet 1064, and also extends from magnet 560 and magnet 1064. There is also a path 2025, which also extends from magnet 560 and magnet 1064. With respect to the embodiment detailed above where the portion of the magnetic path of the magnetic attractive field between the first magnet and the second magnet extends through the recipient to the second magnet passing though at most only carbon based substances, silicon based substances, water based substances, and a metallic coating of the second magnet, this corresponds to the portion of magnetic path that is established by the portion of path 2024 that is below line 2020 (which can represent the surface of the skin).

It is briefly noted that by "passing through at most only" the recited substances, it does not mean that the path/portion of the path must necessarily pass through each of the listed substances. It means that the path/portion of the path does not travel through other substances than those listed.

In an exemplary embodiment of this method, a portion of the magnetic path of the magnetic attractive field between the first magnet and the second magnet extending from a surface of the skin of the recipient (e.g., represented by line 2020) to the first magnet (e.g., magnet 560) passes though only non-metallic substances other than a metallic coating of the first magnet, if present (a metallic coating may not be present). With regard to FIG. 20, the portion of the path is the portion of path 2024 from line 2020 to magnet 560. With respect to this embodiment, by way of example only and not by way of limitation, the magnet 560 can be part of a magnet apparatus that corresponds at least generally to the implanted magnet apparatus/any of the implanted magnet apparatuses detailed above (e.g., magnet 560 is a magnet that is plated with a nickel coating that is encased in a polymer-based housing, etc.). This embodiment is as opposed to, for example, a portion of a path that might extend through the metal of the coil of the external component, or a path that extends through a titanium housing of the external magnet, if such is used.

In an exemplary embodiment, a portion of the magnetic path of the magnetic attractive field between the first magnet and the second magnet extending from a surface of the skin of the recipient to the first magnet (e.g., with respect to FIG. 20, the portion of the path of path 2024 that extends from line 2020 to magnet 560) passes though at most only air, a polymer based material other than a coating of the first magnet, if present, the polymer based coating of the first magnet, if present, and hair, if present. That is, in some instances, there is no polymer based coating of the first magnet (e.g., no polymer housing of the first magnet). In this regard, the first reference to polymer-based material can be the material of the external component, such as a housing thereof, which housing can house electronic components such as the external coil. In an exemplary embodiment, a portion of this housing is the skin interfacing side of the external component/the part that supports the external component against the skin of the recipient. It is noted that the housing of the external component is distinct from any housing of the magnet that might be present. In this regard, in an exemplary embodiment, a housing of the magnet would be a housing that is removed with the magnets upon removal of the magnets from the external component in a housing that is inserted with the magnets upon insertion of the magnets into the external component.

In an exemplary embodiment, the action of establishing or breaking the magnetic attraction includes breaking the magnet attraction, and method further comprises removing the second magnet from the recipient by grasping a projection of a magnet assembly of which the second magnet is a part and providing a withdrawal force thereto. In an exemplary embodiment, the aforementioned method actions are executed after the implantable component is implanted into the recipient. In an exemplary embodiment, this is executed prior to exposing the implantable component to an MRI magnetic field, where the recipient has previously used the implantable component for a period of time.

Consistent with the teachings detailed above, in an exemplary embodiment, the magnet assembly includes a polymer housing encasing the second magnet, and the projection is a monolithic part of the polymer housing.

Also consistent with the teachings detailed above, in an exemplary embodiment, the second magnet is coated with a metallic material, the second magnet and the coating is housed in a housing, the housing is at least partially permeable with respect to body fluids of the recipient, the coating has pin holes therein (and/or, some other imperfection) and body fluids of the recipient are in contact with the second magnet (the implanted magnet—this embodiment discusses the first magnet in terms of the external magnet and the second magnet as the implanted magnet) via the permeability of the housing and the pin holes (and/or other imperfection) of the coating. In an exemplary embodiment, the amount of body fluid that comes into contact with the second magnet over a 24 hour period of full implantation into the recipient after 6 months of implantation is no more than 0.01, 0.02, 0.03, 0.04, 0.05, 0.06, 0.07, 0.08, 0.09, 0.1, 0.15, 0.2, 0.25, 0.3, 0.35, 0.4, 0.5, 0.6, 0.7, 0.8, 0.9, 1.0, 1.25, 1.5, 1.75, 2.0, 2.25, 2.5, 2.75, 3.0, 3.25, 3.5, 3.75, 4.0, 4.25, 4.5, 4.75, or 5% of that which would result in the absence of one of the housing or the coating.

In an exemplary embodiment, the action of establishing or breaking a magnetic attraction between a first magnet of an external component and a second magnet of an implanted component of a prosthesis is executed after the second magnet that has been implanted in the recipient for over H years, where H is 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21, 22, 23, 24, 25, 26, 27, 28, 29, or 30 years or more.

Figure 21:
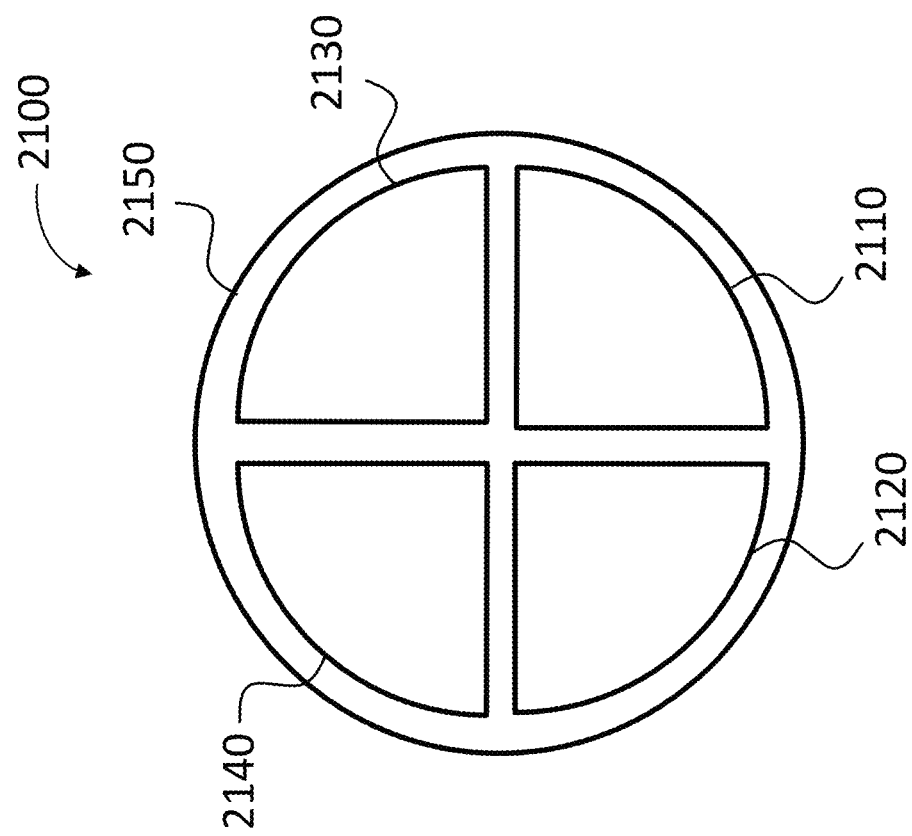
FIGS. 21 and 22 present a schematic of some alternate embodiments of a magnet apparatus.
Figure 22:
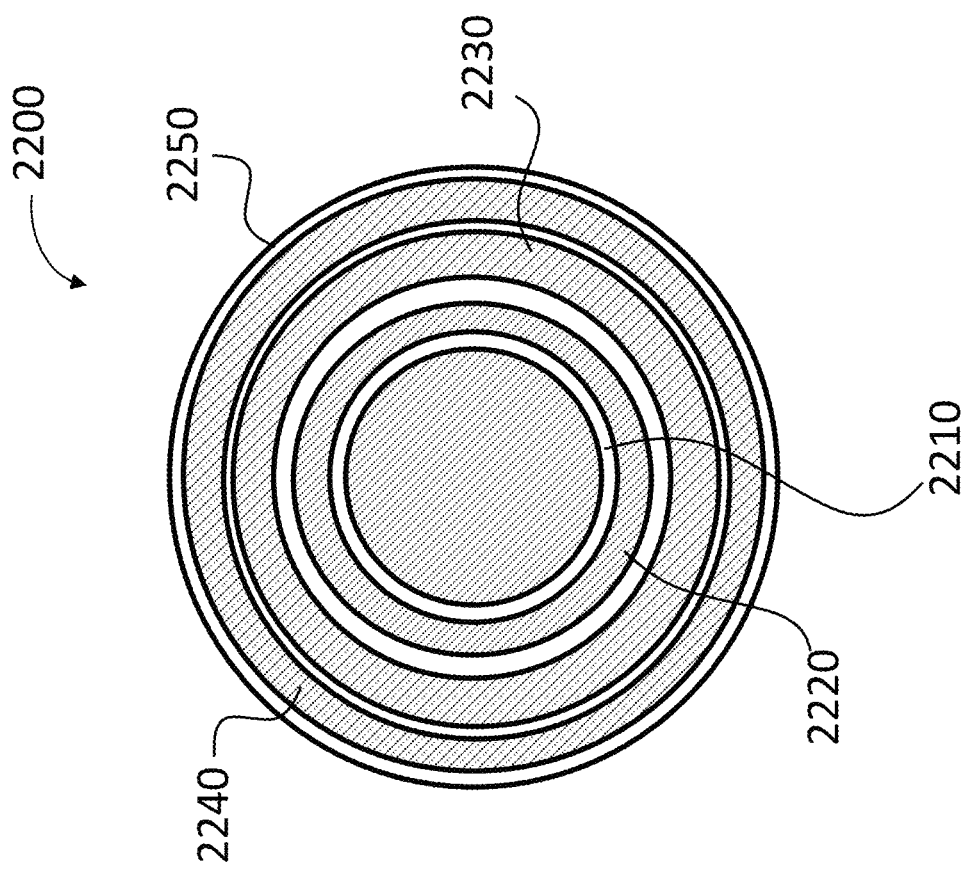

FIGS. 21 and 22 depict an alternate embodiment of a magnet apparatus that is implantable (or can be used in the external device, for that matter). Particularly, FIG. 21 depicts an exemplary magnet apparatus 2100, that includes four magnet portions 2110, 2120, 2130, and 2140. Collectively, these magnet portions are segments of a circular magnet/disk magnet, although in other embodiments, they can be segments of another magnet arrangement. In this embodiment, each of the magnet portions is plated/coated with a metallic substance, such as with any of the coatings detailed herein or any other than can have utilitarian value. All four magnets are encased in a polymer housing 2150. During manufacturing, the magnet segments/magnet portions, which are coated as noted above, are held away from each other and the housing 2150 is molded thereabout in a manner such that the material of the housing also flows/becomes located between the magnet portions. In this regard, polymer is located against, at least in some embodiments, all surfaces of the magnet portions and, polymer is located, at least in some embodiments, at all locations between the magnet portions. In this regard, FIG. 21 depicts polymer located at all locations within the boundaries of the housing 2150 other than the locations of the plated magnets. FIG. 22 depicts an alternate embodiment of a magnet apparatus 2200. Here, concentric magnets 2120, 2220, 2230, and 2240 are arrayed as shown, where, in an exemplary embodiment, each of the magnets is plated/coated with a metallic substance, such as with any of the coatings detailed herein or any other that can have utilitarian value. All four magnets are encased in a polymer housing 2250. During manufacturing, the magnets, which are coated as noted above, are held away from each other and the housing 2250 is molded thereabout in a manner such that the material of the housing also flows/becomes located between the magnet portions. In this regard, polymer is located against, at least in some embodiments, all surfaces of all of the magnets, and polymer is located, at least in some embodiments, at all locations between the magnets. In this regard, FIG. 22 depicts polymer located at all locations within the boundaries of the housing 2250 other than the locations of the plated magnets.

While the embodiments of FIGS. 21 and 22 depict polymer located between the magnets/magnet portions, in an alternate embodiment, there is no polymer located between the magnets/magnet portions, at least not at all locations. In an alternate embodiment, another type of material is located between the magnets/magnet portions, such as a spacer material. That said, in alternate embodiments, there is no polymer located between the magnets/magnet portions. Instead, the magnets/magnet portions are held in place via adhesive or the like located at the tops and the bottoms thereof which adhesive is attached to the top and bottom inner walls of the housing.

It is also noted that the spacing between the magnets/magnet portions can be uniform amongst the components, as is the case in FIG. 21, or be varied/different, as is the case in FIG. 22. It is noted that the spacing between the magnets in FIG. 22 can be uniform in some embodiments, and the spacing between the magnet portions can be varied with respect to the embodiment of FIG. 21. Any arrangement that can enable the teachings detailed herein and/or variations thereof can be utilized in at least some embodiments.

Some embodiments can have utilitarian value with respect to reducing and/or managing eddy current losses associated with the implantable component. In the RF link, the magnet apparatus can be a conductor which reduces the efficiency of the link because eddy currents are induced in the magnet apparatus which cause energy loss. By way of example only and not by way of limitation, in an exemplary embodiment where the implantable magnet apparatus 1160 or 1060 is located inside the inner periphery of the coil 137 of the implantable component, eddy currents can be present, at least when the RF coil is being energized by the external component or otherwise subjected to the inductance field generated by the external component. With the embodiment of magnet apparatus 1060, the eddy currents will occur in the titanium case. In the embodiment of magnet apparatus 1160, eddy currents will occur in the magnet plating material and probably in the magnet 1164 itself. In at least some exemplary embodiments, such occurrences will depend on the thickness of the plating and the skin depth which depends on the RF frequency, etc. The embodiments of FIGS. 21 and 22 can have utilitarian value with respect to reducing eddy current losses because conductor (the magnet) is separated, as seen. In some embodiments, the material located between the magnets/magnet components is an insulator. In an exemplary embodiment, by way of example only and not by way of limitation, without being bound by theory, such can disrupt the eddy current paths and such can have utilitarian result in reduced current flow, and hence reduced losses. With respect to the embodiment of FIG. 21, each quarter of the magnet can be plated as detailed herein, and held slightly apart during molding so the polymer forms an insulation layer between each quarter. Such can also be the case with respect to the embodiment of FIG. 22.

It is noted that other configurations can have utilitarian value with respect to reducing and/or managing eddy currents. Any arrangement that reduces eddy currents, such as any arrangement that utilizes the polymer of the housing to do so or otherwise establish an insulative body or insulative layers between the magnets/magnet components can be utilized in at least some exemplary embodiments.

In an exemplary embodiment, the embodiments of FIGS. 21 and 22 and variations of that concept reduce eddy current losses by at least about 20, 25, 30, 35, 40, 45, 50, 55, 60, 65, 70, 75, 76, 77, 78, 79, 80, 81, 82, 83, 84, 85, 86, 87, 88, 89, 90, 91, 92, 93, 94, 95, 96, 97, 98, or 99% or more relative to that which would be the case if the magnet was a single component (to achieve the same magnetic retention force for apples to apples comparison) and located entirely within the inner perimeter of the coil 137, all things being equal.

It is noted that while the embodiments depicted in FIGS. 21 and 22 show 4 separate magnets/4 separate magnet components, in other embodiments, fewer or more magnets/components can be utilized. In an exemplary embodiment, there are 2, 3, 4, 5, 6, 7, 8, 9, 10, 11, 12, 13, 14, 15, or 16 or more magnets/magnet components. Any arrangement of magnets/magnet components that can enable the teachings detailed herein can be utilized in at least some exemplary embodiments.

In an exemplary embodiment, the magnet is configured to be protected from the body fluids by a barrier consisting of the polymer of the housing 1180 and the metallic substance 1168 or the magnet 1164 is configured to be protected from the body fluids by a barrier consisting essentially of the polymer of the housing 1180 and the metallic substance 1164.

Figure 23:
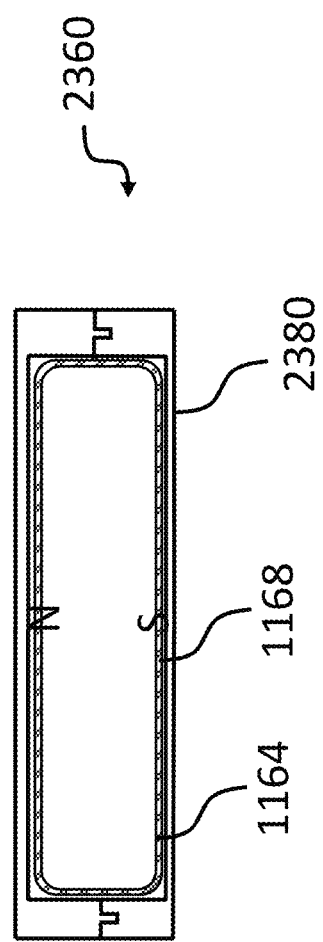
FIGS. 23 and 24 present some additional exemplary embodiments of magnet apparatuses.

It is noted that while the embodiments detailed above have generally concentrated on a housing that is formed via molding about the plated magnet, such as via the use of an injection molding system, some other embodiments entail a housing that is preformed and otherwise snap coupled about the plated magnet (with a sealant in the seam, or with a welding operation performed thereafter to seal the seam—whether such is laser, ultrasonic, vibration, friction, etc.). FIG. 23 depicts an exemplary embodiment of an implantable magnet apparatus 2360, which includes housing 2380 which includes a upper housing sub portion at a lower housing sub portion, which sub portions are snap coupled together to trap the magnet 1164 which is plated via plating 1168 therein. In an exemplary embodiment, an adhesive is located between the seams. It is also noted that the housing 2380 of FIG. 23 represents both a polymer housing and a titanium housing, depending on which embodiment is utilized. Accordingly, some embodiments are such that the housing is not established via separate components/separate sub housings but instead completely molded in one molding operation about the plated magnet.

Figure 24:
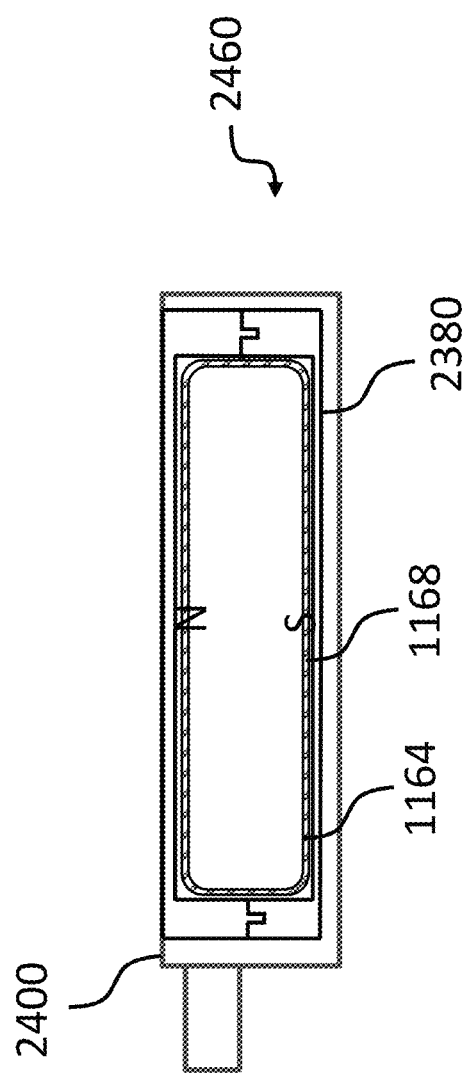

In an exemplary embodiment, there is a method of manufacturing the magnet apparatuses detailed herein and/or variations thereof, which includes plating a permanent magnet or otherwise obtaining a permanent magnet that is plated, wherein the plating can be a Ni coating or the like, or in some embodiments, any plating or any other plating that inhibits or otherwise reduces corrosion during handling, etc. Next, a cassette is molded from PEEK. Next titanium shells are punched and in some embodiments, laser marking is utilized to indicate polarity. Next, finish machining of the shelf faces are executed to obtain a precise fit of the two shells relative to one another. Next, the magnet is glued into one of the shells. Next, the adhesive is permitted to cure or otherwise is cured, after which the shells are placed together and held together. And adhesive is utilized to connect the shells together or, in some embodiments, welding such as laser welding is utilized in, for example, a helium atmosphere, to secure the two shells together. A helium leak test is executed to check for hermeticity of the laser weld. Typically, this is executed within one hour of welding. In some embodiments, a mechanical press is utilized to fit the magnet assembly into the shell. In this regard, in an exemplary embodiment, the magnet apparatus 2360 could be located in a shell 2400, as seen in FIG. 24, where the shell 2400 is made of PEEK, as noted above, and collectively, the magnet apparatus 2360 and the shell 2400 establishes a magnet apparatus 2460 as seen, where the shell includes a tongue as noted above to enable handling or the like.

In another embodiment, there is a method of making a magnet apparatus, which includes plating a permanent magnet with a coating as detailed above, or otherwise obtaining such a magnet, and, subsequently, insert molding with PEEK to mold a housing about the obtained permanent magnet with a coating. In an exemplary embodiment, that is the extent of the method. That said, in an alternate embodiment, a two-step molding process can be executed, where the second step fills gaps where features that held the magnet in place resulted in such during the first step. Accordingly, in an exemplary embodiment, there is a magnet apparatus that includes a housing that has manufacturing holes therethrough which are covered or otherwise filled by filler material which can be the same as the material of the housing, but which can be identified upon a visual inspection or destructive inspection. In an exemplary embodiment, this resulting magnet apparatus (whether made by one or two steps) will be different from the embodiment of FIG. 24, because, in an exemplary embodiment, there will be PEEK or otherwise some other polymer across the top and the bottom of the magnet as opposed to titanium (where, as noted above, in an exemplary embodiment of FIG. 24, the housing 2380 is a titanium housing—in this embodiment, there is no titanium housing or other metallic housing—there is only the magnet, the plating of the magnet, and the polymer there about). In an exemplary embodiment, polarity can be marked by a feature in the mold. In an exemplary embodiment, all the methods detailed herein further include a method of performing a visual and/or other form of inspection and/or a check of the magnet polarity.

In an exemplary embodiment, the magnet apparatuses detailed herein are such that when the magnet apparatus is subjected to a saline test, utilitarian results are present, as will now be detailed. In an exemplary embodiment, the magnet apparatuses are such that when placed in a glass bottle screw top bottle fully immersed in DPBS—(Dulbecco's phosphate-buffered saline (DPBS) is a balanced salt solution—it is considered a good representation of human body fluid), and placed in oven at 60 C, there a no microscopic signs of microscopic (i.e., the inspection is executed using a microscope) for any sign of degradation (e.g. bulges, metallic particles, plastic delamination) after a period of 0.25, 0.5, 0.75, 1, 1.5, 2, 2.5, 3, 4, 5, or 6 months or more that would otherwise indicate that the magnet apparatus is not suitable for implantation in a human being.

It is noted that in at least some embodiments, the metalization/metallic coatings detailed herein are such that there is full metalization of the magnet, and this full metalization does not affect its function, or at least does not reduce the resulting magnetic field in a manner that prevents the magnet from being used. In an exemplary embodiment, the magnetic coatings reduce the magnetic field by no more than 0, 0.25, 0.5, 0.75, 1, 1.5, 2, 2.5, 3, 3.5, 4, 4.5, 5, 5.5, 6, 7, 8, 9, 10, 11, 12, 13, 14, 15, 16, 17, 18 19 or 20% relative to that which was the case in the absence of the coating.

Also, in an exemplary embodiment, the metallic coatings perform most, if not all, of the anti-corrosion functions of the magnet apparatus. In an exemplary embodiment, the metallic coatings reduce corrosion by at least 70, 75, 80, 81, 82, 83, 84, 85, 86, 87, 88, 89, 90, 91, 92, 93, 94, 95, 96, 97, 98, or 99 percent relative to that which would be the case in the absence of the metallic coating all other things being equal.

In some exemplary embodiments, the polymer reduces the ionic and moisture challenge and provides mechanical protection to the metallic coating from a hostile environment that could result in, by way of example only and not by way of limitation, scratches etc.

It is noted that the implantable medical device industry in general, and the hearing prosthesis industry in particular, views the utilization of titanium to encapsulate components that are implanted in a recipient to be essentially the gold standard for implants. Other types of encapsulation which are viewed as having high utilitarian value include stainless steel and ceramic. Encapsulation of components utilizing polymer-based components, such as PEEK or the like, is generally not recommended and generally frowned upon in the aforementioned industries. This is because polymer-based components generally do not establish a hermetic housing. Indeed, in the embodiments detailed above, the housings that are polymer-based or non-ceramic and non-metallic do not form a hermetic housing. That is, the resulting housings are non-hermetic housings.

In at least some exemplary embodiments, the housings detailed herein that are non-ceramic and nonmetallic have relatively high permeability to water vapor. In an exemplary embodiment, the housings detailed herein that are non-ceramic and nonmetallic are at least 30, 40, 50, 60, 70, 75, 80, 81, 82, 83, 84, 85, 86, 87, 88, 89, 90, 91, 92, 93, 94, 95, 96, 97, 98, or 99 percent more permeable to water vapor and/or to the aforementioned DPBS over a 2, 3, 4, 5, or 6 week period at 60 C per cubic millimeter of material than ceramic and/or titanium housings. That is, by way of example only and not by way of limitation, if a housing having the a wall thickness was made out of the various components, the housing utilizing the non-ceramic and nonmetallic components have the aforementioned features relative to the housing made of ceramic and/or titanium with that exact same wall thickness (for an apples to apples comparison).

In an exemplary embodiment there is an implantable prosthesis, comprising: an implantable component including an implantable magnet assembly, wherein the magnet assembly includes a magnet plated with a metallic substance, the magnet assembly includes a housing made at least in part of a polymer, wherein the magnet is located in the housing, wherein at least a portion of the housing made out of the polymer is in direct contact with the metallic substance, and the implantable component is configured to be implanted in a human such that the housing is exposed to body fluids thereof. In an exemplary embodiment of this embodiment, the prosthesis further comprises a second magnet plated with a metallic substance, wherein the second magnet is located within the housing, wherein at least a portion of the housing made out of the polymer is in direct contact with the metallic substance of the second magnet, and the magnet and the second magnet are separated from one another by the polymer of the housing.

In an exemplary embodiment, there is an implantable magnet assembly, comprising: a magnet coated with a substance, the magnet being located in a housing, wherein the implantable magnet assembly is configured to be implanted in a human such that the housing is exposed to body fluids thereof, and the assembly is configured to protect the magnet from body fluids via a system that consists of the substance that coats the magnet and one or more non-metallic pliable components. In an embodiment of this embodiment, the housing is a polymer molded component that includes a grip tongue that is monolithic with a portion of the housing that encapsulates the magnet. In an exemplary embodiment, there is a method that includes establishing or breaking a magnetic attractive field between a first magnet of an external component of a prosthesis and a second magnet of an implanted component of the prosthesis, a portion of a magnetic path of the magnetic attractive field between the first magnet and the second magnet that extends through the recipient to the second magnet passing though at most only carbon based substances, silicon based substances, air, water based substances, and a metallic coating of the second magnet. In an embodiment of this embodiment, the action of establishing or breaking a magnetic attraction between a first magnet of an external component and a second magnet of an implanted component of a prosthesis is executed after the second magnet that has been implanted in the recipient for over 5 years.

It is noted that any method detailed herein also corresponds to a disclosure of a device and/or system configured to execute one or more or all of the method actions detailed herein. It is further noted that any disclosure of a device and/or system detailed herein corresponds to a method of making and/or using that the device and/or system, including a method of using that device according to the functionality detailed herein.

It is further noted that any disclosure of a device and/or system detailed herein also corresponds to a disclosure of otherwise providing that device and/or system.

It is noted that in at least some exemplary embodiments, any feature disclosed herein can be utilized in combination with any other feature disclosed herein unless otherwise specified. Accordingly, exemplary embodiments include a medical device including one or more or all of the teachings detailed herein, in any combination.

Note that exemplary embodiments include components detailed herein and in the figures that are rotationally symmetric about an axis thereof (e.g., the magnet apparatus 160). Accordingly, any disclosure herein corresponds to a disclosure in an alternate embodiment of a rotationally symmetric component about an axis thereof. Moreover, the exemplary embodiments include components detailed in the figures that have cross-sections that are constant in and out of the plane of the figure. Thus, the magnet apparatus 160 can correspond to a bar or box magnet apparatus, etc.).

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. An implantable prosthesis, comprising:
an implantable component including an implantable magnet assembly, wherein
the magnet assembly includes a magnet plated with a metallic substance,
the magnet assembly includes a housing made at least in part of a polymer, wherein the magnet is located in the housing, wherein at least a portion of the housing made out of the polymer is in direct contact with the metallic substance, and
the implantable component is configured to be implanted in a human such that the housing is exposed to body fluids thereof.

2. The implantable prosthesis of claim 1, wherein:
the magnet is covered by plating established by the metallic substance, the plating having pin holes therein.

3. The implantable prosthesis of claim 1, wherein:
the magnet is made of a material that readily corrodes when exposed to body fluids.

4. The implantable prosthesis of claim 1, wherein:
the magnet is configured to be protected from the body fluids by a barrier consisting of the polymer of the housing and the metallic substance.

5. The implantable prosthesis of claim 1, wherein:
the magnet is configured to be protected from the body fluids by a barrier consisting essentially of the polymer of the housing and the metallic substance.

6. The implantable prosthesis of claim 1, wherein:
the magnet is made of a rare earth material, such as, for example, NdFeB or SmCo.

7. The implantable prosthesis of claim 1, wherein:
the implantable magnet assembly is devoid of metals and ceramic materials covering the plating established by the metallic substance.

8. The implantable prosthesis of claim 1, wherein:
the implantable magnet assembly is configured to be removably inserted into an implantable portion of a hearing prosthesis.

9. An implantable prosthesis, comprising:
an implantable functional component including an implantable first housing and an implantable magnet assembly, the first housing having electronics located therein, wherein
the magnet assembly includes a plated magnet located in a second housing,
the second housing is established by structural components that are carbon or silicone chain based components, and
the magnet assembly includes only one housing, the only one housing corresponding to the second housing.

10. The implantable prosthesis of claim 9, wherein:
the second housing consists essentially of a polymer.

11. The implantable prosthesis of claim 9, wherein:
the second housing is in direct contact with the plating of the magnet.

12. The implantable prosthesis of claim 9, wherein:
the magnet assembly is supported in the implantable prosthesis via a silicone body supporting the housing and the first housing, wherein the magnet assembly is devoid of metallic components other than the magnet and the plating thereof and is devoid of ceramic materials.

13. The implantable prosthesis of claim 9, wherein:
the magnet assembly is supported in the implantable prosthesis via a silicone body that also supports an RF inductance coil, wherein with respect to components of the implantable prosthesis located inboard of the RF inductance coil and outboard of the plated magnet, the components have a hardness of less than 80 A on the Shore A scale.

14. The implantable prosthesis of claim 9, wherein:
the implantable prosthesis is configured to enable the magnet assembly to be removed, as a complete assembly, from the implantable functional component while the implantable functional component is implanted in the recipient.

15. A prosthesis system, comprising:
the implantable prosthesis of claim 9; and
an external component including a first RF inductance coil and a second magnet assembly including a second magnet concentrically located within the first RF inductance coil, wherein
the plated magnet of the magnet assembly is concentric with a second RF inductance coil of the implantable functional component,
the prosthesis system is configured to establish inductance communication between the first RF inductance coil and the second RF inductance coil,
the prosthesis system is configured to establish a magnetic coupling between the second magnet and the plated magnet so as to place the second RF inductance coil of the external component in a substantially concentric orientation with the first RF inductance coil of the implantable functional component via a magnetic field path extending from the surface of the plated magnet to the surface of the second magnet assembly that passes through at most only carbon based substances, silicon based substances, water based substances and air.

16. The prosthesis system of claim 15, wherein:
the second magnet is plated; and
the magnetic field path extending from the plated magnet to the second magnet extends from the plating of the plated magnet to the plating of the second magnet without passing through a metallic component.

17. An implantable magnet assembly, comprising:
a magnet coated with a substance, the magnet being located in a housing, wherein
the implantable magnet assembly is configured to be implanted in a human such that the housing is exposed to body fluids thereof, and
the assembly is configured to protect the magnet from body fluids via a system that consists of the substance that coats the magnet and one or more non-metallic pliable components.

18. The implantable magnet assembly of claim 17, wherein:
the implantable magnet assembly consists of the magnet and the housing.

19. The implantable magnet assembly of claim 17, wherein:
the housing is made of a non-metallic, non-ceramic, substance.

20. The implantable magnet assembly of claim 17, wherein:
the substance coating the magnet is nickel based plating.

21. The implantable magnet assembly of claim 17, wherein:
the assembly is configured to protect the magnet from body fluids via a system that consists of the substance that coats the magnet and the housing.

22. The implantable magnet assembly of claim 17, wherein:
other than the magnet and the substance that coats the magnet, the implantable magnet assembly is devoid of metallic components.

23. The implantable magnet assembly of claim 17, wherein:
the implantable magnet assembly is devoid of ceramic components.

24. The implantable magnet assembly of claim 17, further comprising:
a silicone body surrounding the system that consists of the substance that coats the magnet and one or more non-metallic pliable components.

25. A method, comprising:
establishing or breaking a magnetic attractive field between a first magnet of an external component of a prosthesis and a second magnet of an implanted component of the prosthesis, a portion of a magnetic path of the magnetic attractive field between the first magnet and the second magnet that extends through the recipient to the second magnet passing though at most only carbon based substances, silicon based substances, air, and water based substances, in addition to also passing through a metallic coating of the second magnet.

26. The method of claim 25, wherein:
a portion of the magnetic path of the magnetic attractive field between the first magnet and the second magnet that extends from a surface of the skin of the recipient to the first magnet passes though only non-metallic substances other than a metallic coating of the first magnet, if present.

27. The method of claim 26, wherein:
a portion of the magnetic path of the magnetic attractive field between the first magnet and the second magnet extending from a surface of the skin of the recipient to the first magnet passes though at most only air, a polymer based material other than a coating of the first magnet, if present, the polymer based material of the coating of the first magnet, if present, and hair, if present.

28. The method of claim 26, wherein:
the action of establishing or breaking the magnetic attraction includes breaking the magnet attraction; and
the method further comprises:
removing the second magnet from the recipient by grasping a projection of a magnet assembly of which the second magnet is a part and providing a withdrawal force thereto.

29. The method of claim 28, wherein:
the magnet assembly includes a polymer housing encasing the second magnet; and
the projection is a monolithic part of the polymer housing.

30. The method of claim 26, wherein:
the second magnet is coated with a metallic material;
the second magnet and the coating is housed in a housing;
the housing is at least partially permeable with respect to body fluids of the recipient;
the coating has pin holes therein; and
body fluids of the recipient are in contact with the second magnet via the permeability of the housing and the pin holes of the coating.

31. The method of claim 26, wherein:
the action of establishing or breaking a magnetic attraction between a first magnet of an external component and a second magnet of an implanted component of a prosthesis is executed after the second magnet that has been implanted in the recipient for over 1 year.

* * * * *